US010653826B2

(12) United States Patent
Kelly et al.

(10) Patent No.: US 10,653,826 B2
(45) Date of Patent: *May 19, 2020

(54) BLOOD TREATMENT AIR PURGING SYSTEMS

(71) Applicants: Baxter International Inc., Deerfield, IL (US); Baxter Healthcare SA, Glattpark (Opfikon) (CH)

(72) Inventors: Thomas D. Kelly, Highland Park, IL (US); Marc S. Minkus, Bannockburn, IL (US); Angelito A. Bernardo, River Forest, IL (US); William P. Burns, Channahon, IL (US); Robert W. Childers, New Port Richey, IL (US); Shincy J. Maliekkal, Glenview, IL (US); Matthew R. Muller, Lindenhurst, IL (US); Justin B. Rohde, Des Plaines, IL (US); Michael E. Hogard, Odessa, FL (US)

(73) Assignees: Baxter International Inc., Deerfield, IL (US); Bazter Healthcare SA, Glattpark (Opfikon) (CH)

( * ) Notice: Subject to any disclaimer, the term of this patent is extended or adjusted under 35 U.S.C. 154(b) by 187 days.

This patent is subject to a terminal disclaimer.

(21) Appl. No.: 15/789,535

(22) Filed: Oct. 20, 2017

(65) Prior Publication Data

US 2018/0036472 A1    Feb. 8, 2018

Related U.S. Application Data

(63) Continuation of application No. 14/446,609, filed on Jul. 30, 2014, now Pat. No. 9,795,731, which is a
(Continued)

(51) Int. Cl.
*A61M 1/36* (2006.01)
*A61M 1/28* (2006.01)
*A61M 1/16* (2006.01)

(52) U.S. Cl.
CPC ............ *A61M 1/3643* (2013.01); *A61M 1/16* (2013.01); *A61M 1/1601* (2014.02);
(Continued)

(58) Field of Classification Search
CPC .. A61M 1/3643; A61M 1/1601; A61M 1/282; A61M 1/288; A61M 1/3644;
(Continued)

(56) References Cited

U.S. PATENT DOCUMENTS 250,868 A    12/1881    Abbott
927,476 A    7/1909    Barker
(Continued)

FOREIGN PATENT DOCUMENTS

CH    296007    1/1954
DE    1806654    5/1970
(Continued)

OTHER PUBLICATIONS

International Search Report and Written Opinion of the International Searching Authority for International Application No. PCT/US2008/080166 dated Jan. 20, 2009.
(Continued)

*Primary Examiner* — Philip R Wiest
(74) *Attorney, Agent, or Firm* — K&L Gates LLP

(57) ABSTRACT

Dialysis systems that remove air from a blood circuit are disclosed herein. In an embodiment, a dialysis system includes a dialysis fluid circuit, a blood circuit including an arterial line, a venous line, and an enclosure in fluid communication with the venous line, the enclosure configured to release air through a hydrophobic vent for priming the blood
(Continued)

circuit, a blood pump configured to pump fluid through at least the arterial line, a first valve operable with the arterial line and a second valve operable with the venous line, and a pumping and valving algorithm operated after priming to remove air from the blood circuit to control the first and second valves and the blood pump to replace priming fluid with blood from a patient.

20 Claims, 18 Drawing Sheets

Related U.S. Application Data continuation of application No. 13/894,020, filed on May 14, 2013, now Pat. No. 8,834,403, which is a continuation of application No. 12/237,160, filed on Sep. 24, 2008, now Pat. No. 8,444,587.

(60) Provisional application No. 60/976,731, filed on Oct. 1, 2007.

(52) U.S. Cl.
CPC ............ *A61M 1/282* (2014.02); *A61M 1/288* (2014.02); *A61M 1/3624* (2013.01); *A61M 1/3627* (2013.01); *A61M 1/3644* (2014.02); *A61M 1/3649* (2014.02); *A61M 2202/02* (2013.01); *A61M 2202/0413* (2013.01); *A61M 2205/10* (2013.01); *A61M 2205/3382* (2013.01); *A61M 2205/3386* (2013.01); *A61M 2205/75* (2013.01); *Y10T 137/0402* (2015.04)

(58) Field of Classification Search
CPC .... A61M 1/3649; A61M 1/16; A61M 1/3624; A61M 1/3627; A61M 2202/02; A61M 2202/0413; A61M 2205/10
See application file for complete search history.

(56) References Cited

U.S. PATENT DOCUMENTS

| | | |
|---|---|---|
| 1,505,050 A | 8/1924 | Lauritsen |
| 2,292,007 A | 8/1942 | Morgan |
| 3,044,236 A | 7/1962 | Bearden et al. |
| 3,074,645 A | 1/1963 | Main |
| 3,095,062 A | 6/1963 | Neely |
| 3,229,445 A | 1/1966 | Kraft |
| 3,287,885 A | 11/1966 | Sommer |
| 3,295,297 A | 1/1967 | Collins |
| 3,342,019 A | 9/1967 | Smythe |
| 3,412,760 A | 11/1968 | Franck |
| 3,527,572 A | 9/1970 | Urkiewicz |
| 3,581,464 A | 6/1971 | Bhuta et al. |
| 3,598,727 A | 8/1971 | Wilock |
| 3,677,710 A | 7/1972 | Hirsch |
| 3,744,492 A | 7/1973 | Leibinsohn |
| 3,756,234 A | 9/1973 | Kopp |
| 3,769,207 A | 10/1973 | Baer |
| 3,771,288 A | 11/1973 | Wisman et al. |
| 3,795,088 A | 3/1974 | Esmond |
| 3,827,561 A | 8/1974 | Serfass et al. |
| 3,830,234 A | 8/1974 | Kopp |
| 3,834,386 A | 9/1974 | Sisley |
| 3,849,071 A | 11/1974 | Kayser |
| 3,908,653 A | 9/1975 | Kettering |
| 3,964,479 A | 6/1976 | Boag et al. |
| 3,976,311 A | 8/1976 | Spendlove |
| 3,985,134 A | 10/1976 | Lissot et al. |
| 3,996,027 A | 12/1976 | Schnell et al. |
| 4,031,891 A | 6/1977 | Jess |
| 4,038,190 A | 7/1977 | Baudet et al. |
| 4,047,563 A | 9/1977 | Kurata |
| 4,048,995 A | 9/1977 | Mittleman |
| 4,054,522 A | 10/1977 | Pinkerton |
| 4,061,031 A | 12/1977 | Grimsrud |
| 4,102,655 A | 7/1978 | Jeffrey et al. |
| 4,137,160 A | 1/1979 | Ebing et al. |
| 4,149,860 A | 4/1979 | Kulik |
| 4,151,088 A | 4/1979 | Wolf, Jr. et al. |
| 4,191,182 A | 3/1980 | Popovich et al. |
| 4,200,095 A | 4/1980 | Reti |
| 4,293,413 A | 10/1981 | Schnell |
| 4,304,670 A | 12/1981 | Watanabe et al. |
| 4,311,137 A | 1/1982 | Gerard |
| 4,325,715 A | 4/1982 | Bowman et al. |
| 4,332,264 A | 6/1982 | Gortz |
| 4,344,777 A | 8/1982 | Siposs |
| 4,345,919 A | 8/1982 | Wilkinson et al. |
| 4,345,999 A | 8/1982 | Sigdell et al. |
| 4,353,368 A | 10/1982 | Slovak et al. |
| 4,363,641 A | 12/1982 | Finn, III |
| 4,368,118 A | 1/1983 | Siposs |
| 4,427,009 A | 1/1984 | Wells et al. |
| 4,433,971 A | 2/1984 | Lindsay et al. |
| 4,464,172 A | 8/1984 | Lichtenstein |
| 4,486,188 A | 12/1984 | Altshuler et al. |
| 4,493,705 A | 1/1985 | Gordon et al. |
| 4,512,163 A | 4/1985 | Wells et al. |
| 4,531,937 A | 7/1985 | Yates |
| 4,568,333 A | 2/1986 | Sawyer et al. |
| 4,583,981 A | 4/1986 | Urquhart et al. |
| 4,586,925 A | 5/1986 | Carlsson et al. |
| 4,622,032 A | 11/1986 | Katsura et al. |
| 4,643,713 A | 2/1987 | Viitala |
| 4,643,715 A | 2/1987 | Isono et al. |
| 4,666,598 A | 5/1987 | Heath et al. |
| 4,681,606 A | 7/1987 | Swan, Jr. et al. |
| 4,722,725 A | 2/1988 | Sawyer et al. |
| 4,722,731 A | 2/1988 | Vailancourt |
| 4,734,269 A | 3/1988 | Clarke et al. |
| 4,806,135 A | 2/1989 | Siposs |
| 4,923,612 A | 5/1990 | Trivett et al. |
| 4,932,987 A | 6/1990 | Molina |
| 4,941,875 A | 7/1990 | Brennan |
| 4,946,439 A | 8/1990 | Eggers |
| D311,061 S | 10/1990 | Vrana et al. |
| 4,976,685 A | 12/1990 | Block, Jr. |
| 4,997,464 A | 3/1991 | Kopf |
| 5,047,147 A | 9/1991 | Chevallet et al. |
| 5,049,492 A | 9/1991 | Sauer et al. |
| 5,059,173 A | 10/1991 | Sacco |
| 5,061,236 A | 10/1991 | Sutherland et al. |
| 5,061,365 A | 10/1991 | Utterberg |
| 5,112,480 A | 5/1992 | Hukasawa |
| 5,167,921 A | 12/1992 | Gordon |
| 5,178,763 A | 1/1993 | Delaunay |
| 5,204,000 A | 4/1993 | Steadman et al. |
| 5,228,889 A | 7/1993 | Cortial et al. |
| 5,246,560 A | 9/1993 | Nekoksa et al. |
| 5,259,961 A | 11/1993 | Eigendorf |
| 5,268,077 A | 12/1993 | Bubik et al. |
| 5,328,461 A | 7/1994 | Utterberg |
| 5,336,165 A | 8/1994 | Twardowski |
| 5,356,376 A | 10/1994 | Milijasevic et al. |
| 5,358,481 A | 10/1994 | Todd et al. |
| 5,368,555 A | 11/1994 | Sussman et al. |
| 5,394,732 A | 3/1995 | Johnson et al. |
| 5,411,705 A | 5/1995 | Thor et al. |
| 5,421,815 A | 6/1995 | Noguchi et al. |
| 5,429,595 A | 7/1995 | Wright, Jr. et al. |
| 5,441,636 A | 8/1995 | Chevallet et al. |
| 5,468,388 A | 11/1995 | Goddard et al. |
| 5,484,397 A | 1/1996 | Twardowski |
| 5,489,385 A | 2/1996 | Raabe et al. |
| 5,490,925 A | 2/1996 | Eigendorf |
| 5,503,801 A | 4/1996 | Brugger |
| 5,509,895 A | 4/1996 | Noguchi et al. |
| 5,520,640 A | 5/1996 | Utterberg |
| 5,578,070 A | 11/1996 | Utterberg |
| 5,591,251 A | 1/1997 | Brugger |
| 5,605,540 A | 2/1997 | Utterberg |

(56) References Cited

U.S. PATENT DOCUMENTS

| | | | |
|---|---|---|---|
| 5,637,081 A | 6/1997 | Noguchi et al. | |
| 5,643,205 A | 7/1997 | Utterberg | |
| 5,650,071 A | 7/1997 | Brugger et al. | |
| 5,674,199 A | 10/1997 | Brugger | |
| 5,681,294 A | 10/1997 | Osborne et al. | |
| 5,683,355 A | 11/1997 | Fini et al. | |
| 5,690,831 A * | 11/1997 | Kenley | A61L 2/04 210/646 |
| 5,702,606 A | 12/1997 | Peter, Jr. et al. | |
| 5,725,776 A | 3/1998 | Kenley et al. | |
| 5,730,730 A | 3/1998 | Darling, Jr. | |
| 5,763,266 A | 6/1998 | Palsson et al. | |
| 5,776,091 A | 7/1998 | Brugger et al. | |
| 5,776,345 A | 7/1998 | Truitt et al. | |
| 5,800,597 A | 9/1998 | Perrotta et al. | |
| 5,830,185 A | 11/1998 | Block, Jr. | |
| 5,849,065 A | 12/1998 | Wojke | |
| 5,851,202 A | 12/1998 | Carlsson | |
| 5,858,239 A | 1/1999 | Kenley et al. | |
| 5,863,421 A | 1/1999 | Peter, Jr. et al. | |
| 5,895,368 A | 4/1999 | Utterberg | |
| 5,902,476 A | 5/1999 | Twardowski | |
| 5,910,252 A | 6/1999 | Truitt et al. | |
| 5,928,889 A | 7/1999 | Bakich et al. | |
| 5,931,990 A | 8/1999 | Andrews | |
| 5,932,103 A | 8/1999 | Kenley et al. | |
| 5,948,251 A | 9/1999 | Brugger | |
| 5,951,870 A | 9/1999 | Utterberg | |
| 5,980,741 A | 11/1999 | Schnell et al. | |
| 5,983,947 A | 11/1999 | Utterberg | |
| 5,989,318 A | 11/1999 | Schroll | |
| 6,010,623 A | 1/2000 | Schnell et al. | |
| 6,019,824 A | 2/2000 | Schnell | |
| 6,046,806 A | 4/2000 | Thompson | |
| 6,051,134 A | 4/2000 | Schnell et al. | |
| 6,053,967 A | 4/2000 | Heilmann et al. | |
| 6,066,111 A | 5/2000 | Brockhoff | |
| 6,071,269 A | 6/2000 | Schnell et al. | |
| 6,117,342 A | 9/2000 | Schnell et al. | |
| 6,132,616 A | 10/2000 | Twardowski et al. | |
| 6,146,536 A | 11/2000 | Twardowski | |
| 6,171,484 B1 | 1/2001 | Schnell et al. | |
| 6,176,903 B1 | 1/2001 | Wamsiedler | |
| 6,187,198 B1 | 2/2001 | Utterberg | |
| 6,206,954 B1 | 3/2001 | Schnell et al. | |
| 6,251,167 B1 | 6/2001 | Berson | |
| 6,274,034 B1 | 8/2001 | Nikaido et al. | |
| 6,312,414 B1 | 11/2001 | Brockhoff et al. | |
| 6,331,252 B1 | 12/2001 | El Sayyid et al. | |
| 6,344,139 B1 | 2/2002 | Utterberg | |
| 6,357,600 B1 | 3/2002 | Scagliarini | |
| 6,391,541 B1 | 5/2002 | Petersen et al. | |
| 6,391,638 B1 | 5/2002 | Shaaltiel | |
| 6,464,878 B2 | 10/2002 | Utterberg | |
| 6,481,455 B2 | 11/2002 | Gustafson et al. | |
| 6,491,656 B1 | 12/2002 | Morris | |
| 6,514,255 B1 | 2/2003 | Ferree | |
| 6,537,356 B1 | 3/2003 | Soriano | |
| 6,551,513 B2 | 4/2003 | Nikaido et al. | |
| 6,558,340 B1 | 5/2003 | Traeger | |
| 6,561,997 B1 | 5/2003 | Weitzel et al. | |
| 6,562,107 B2 | 5/2003 | Purdom et al. | |
| 6,572,576 B2 | 6/2003 | Brugger et al. | |
| 6,582,604 B2 | 6/2003 | Nikaido et al. | |
| 6,595,948 B2 | 7/2003 | Suzuki et al. | |
| 6,755,801 B2 | 6/2004 | Utterberg et al. | |
| 6,827,862 B1 | 12/2004 | Brockhoff et al. | |
| 6,830,553 B1 | 12/2004 | Burbank et al. | |
| 7,040,142 B2 | 5/2006 | Burbank | |
| 7,087,033 B2 | 8/2006 | Brugger et al. | |
| 7,097,690 B2 | 8/2006 | Usher et al. | |
| 7,169,352 B1 | 1/2007 | Felt et al. | |
| 7,186,342 B2 | 3/2007 | Pirazzoli et al. | |
| 7,214,312 B2 | 5/2007 | Brugger et al. | |
| 2001/0042441 A1 | 11/2001 | Purdom et al. | |
| 2002/0007137 A1 * | 1/2002 | Utterberg | A61M 1/3639 604/4.01 |
| 2004/0019313 A1 | 1/2004 | Childers et al. | |
| 2005/0131332 A1 * | 6/2005 | Kelly | A61M 1/1696 604/4.01 |
| 2006/0213835 A1 | 9/2006 | Nimura et al. | |
| 2009/0101550 A1 | 4/2009 | Muller et al. | |

FOREIGN PATENT DOCUMENTS

| | | |
|---|---|---|
| DE | 3442744 | 6/1986 |
| EP | 0 058 325 | 8/1982 |
| EP | 0 106 026 | 4/1984 |
| EP | 0 143 340 | 6/1985 |
| EP | 0 318 993 | 6/1989 |
| EP | 0 350 675 | 1/1990 |
| EP | 0 501 144 | 1/1992 |
| EP | 560368 A2 | 9/1993 |
| EP | 0 587 251 | 3/1994 |
| EP | 720856 A2 | 7/1996 |
| EP | 560368 B1 | 2/1998 |
| EP | 826383 A2 | 3/1998 |
| EP | 826384 A2 | 3/1998 |
| EP | 720856 B1 | 10/2001 |
| EP | 826384 B1 | 10/2001 |
| EP | 0 776 222 | 4/2003 |
| EP | 1323439 A2 | 7/2003 |
| EP | 1323439 A3 | 8/2003 |
| EP | 826383 B1 | 8/2004 |
| GB | 1 408 319 | 10/1975 |
| GB | 1 554 810 | 10/1979 |
| GB | 2 061 755 | 5/1981 |
| GB | 2 212 739 | 8/1989 |
| GR | 3026703 | 7/1998 |
| WO | 98/23353 | 6/1998 |

OTHER PUBLICATIONS

International Search Report and Written Opinion of the International Searching Authority for International Application No. PCT/US2008/077668 dated Jan. 13, 2009.

European Office Action dated Nov. 5, 2014 for related European Appln. No. 08850086.3 (3 pages).

* cited by examiner

BLOOD TREATMENT AIR PURGING SYSTEMS

PRIORITY CLAIM

The present application is a continuation of U.S. application Ser. No. 14/446,609, entitled "Blood Treatment Air Purging Methods", filed Jul. 30, 2014, which is a continuation of U.S. application Ser. No. 13/894,020, entitled "Fluid and Air Handling in Blood and Dialysis Circuits", filed May 14, 2013, now U.S. Pat. No. 8,834,403, issued Sep. 16, 2014, which is a continuation of U.S. application Ser. No. 12/237,160, entitled "Fluid and Air Handling in Blood and Dialysis Circuits", filed on Sep. 24, 2008, now U.S. Pat. No. 8,444,587, issued May 21, 2013, which claims priority to and the benefit of U.S. Provisional Patent Application Ser. No. 60/976,731, filed Oct. 1, 2007, entitled "Fluid And Air Handling In Dialysis Circuit Air Removal System", the disclosure if each of which is incorporated herein by reference and relied upon.

BACKGROUND

The examples discussed below relate generally to medical fluid delivery. More particularly, the examples disclose systems, methods and apparatuses for dialysis, such as hemodialysis ("HD"), hemofiltration ("HF") hemodiafiltration ("HDF") automated peritoneal dialysis ("APD").

Due to various causes, a person's kidneys can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate to cause diffusion. Hemofiltration ("HF") is an alternative renal replacement therapy that relies on a convective transport of toxins from patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that a patient receiving more frequent treatments removes more toxins and waste products than a patient receiving less frequent but perhaps longer treatments. Studies on HHD have shown a reduction in anti-hypertensive medications while restoring normotension. Randomized trials on long daily dialysis have shown a reduction in left ventricular hypertrophy, which is a surrogate marker for improved patient survival. In addition a patient receiving more frequent treatments does not experience as much of a down cycle as does an in-center patient who has built-up two or three days worth of toxins prior to a treatment, providing much better quality of life. In certain areas, the closest dialysis center can be many miles from the patient's home causing door-to-door treatment time to consume a large portion of the day. HHD can take place overnight or during the day while the patient relaxes, works or is otherwise productive.

Another type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. Osmotic agent in dialysis provides the osmotic gradient. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain to allow spent dialysate fluid to drain from the peritoneal cavity. The patient then connects the catheter to a bag of fresh dialysate to infuse fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter and into the patient's peritoneal cavity. APD machines also allow for the dialysate to dwell within the cavity and for the transfer of waste, toxins and excess water to take place. The source can include multiple sterile dialysate solution bags.

APD machines pump spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In any of the above modalities, entrained air and other gases are a concern. Entrained air can cause inaccuracies when pumping dialysate for either PD or HD. Entrained air can cause a reduction in effective surface area in a hemodialysis filter when it accumulates on the filter fibers, leading to a reduction in the effectiveness of the therapy. Entrained air entering a patient's peritoneum during PD can cause discomfort. Entrained air entering a patient's bloodstream during HD can have severe consequences. Even though the patient may be protected from an air embolism in some HD equipment, there have been situations with removing the air from the blood in which the patient has had to throw away the extracorporeal circuit, resulting in blood loss and cost. Accordingly, a need exists to provide an apparatus that ensures that entrained air is removed from dialysate or blood prior to delivering such fluids to the patient.

SUMMARY

The present disclosure may employ level sensing and coordinated pumping and valving algorithms to control the fluid level in an air trap. In addition, the present disclosure allows the system to flow either gas or fluid (saline and/or heparin and/or priming solution and/or dialysis solution and/or blood and/or etc.) out of a fluid circuit directly to a fluid drain and/or fluid vessel (i.e. saline bag and/or priming bag and/or dialysis solution bag and/or container). Also, the present disclosure allows the system to flow gas out of a fluid circuit directly to atmosphere and fluid (saline and/or heparin and/or priming solution and/or dialysis solution and/or blood and/or etc.) out of a fluid circuit directly to a fluid drain and/or fluid vessel (i.e. saline bag and/or priming bag and/or dialysis solution bag and/or container).

The method of controlling level and removing air described above has advantages in the areas of priming and air trap level control. Currently air trap level control is a manual process. Prior to the therapy, the operator must connect a port on the air trap to a luer connection on the instrument. This port connects the air trap to a compressor on the instrument. This in turn allows for lowering or raising the air trap fluid level through level control switches on the instrument. If the operator does not make this connection securely, blood can flow up through this port and into the instrument during the therapy placing the patient at risk for blood loss and/or blood contamination. In other devices the patient attaches a syringe to the extracorporeal circuit to try to draw air out of the circuit. Because of the pressurization of the circuit blood loss can occur if the tubing is not closed properly after withdrawing air and there is also the risk of blood contamination during the manual procedure. The present disclosure eliminates these risks because the level control mechanism does not require the operator to make any connections.

During prime, the operator must monitor the fluid level in the air trap and manually raise this level to remove air from the extracorporeal circuit. During therapy, the operator must continue to monitor the fluid level in the air trap. If the operator fails to properly maintain the fluid level and lets this level drop to where air is able to pass through the air trap the patient is at risk for an air embolism. The air trap level changes with changes in fluid pressure, making frequent monitoring of the fluid level in the air trap important. The present disclosure removes both of those failure causes by using automatic level sensing to determine when action needs to be taken to raise the level and uses pump and valve configurations to automatically purge the air.

In addition, the present disclosure allows the priming solution from the extracorporeal circuit to be dumped to the drain. Currently the priming solution is either returned to the patient or purged to a waste container. Each of these methods have risks. If the priming solution is returned to the patient, it may return harmful substances that were released from the disposable kit and/or dialyzer during the prime, to the patient. If the priming solution is sent to a waste container, there is a risk that the patient may lose a significant amount of blood if the operator does not stop the purge at the appropriate time. With the current method of sending prime solution to a waste container, the operator connects the arterial bloodline to the patient's arterial access site. The venous line remains disconnected while the instrument draws blood from the patient and displaces priming fluid from the venous line into a waste container or rinse bucket. If the operator fails to stop the blood pump and connect the venous line to the patient when blood reaches the end of the venous bloodline, significant blood loss may result.

It is accordingly an advantage to provide improved systems and methods for the removal of air from dialysis systems.

Additional features and advantages are described herein, and will be apparent from, the following Detailed Description and the figures.

DETAILED DESCRIPTION

Figure 1:
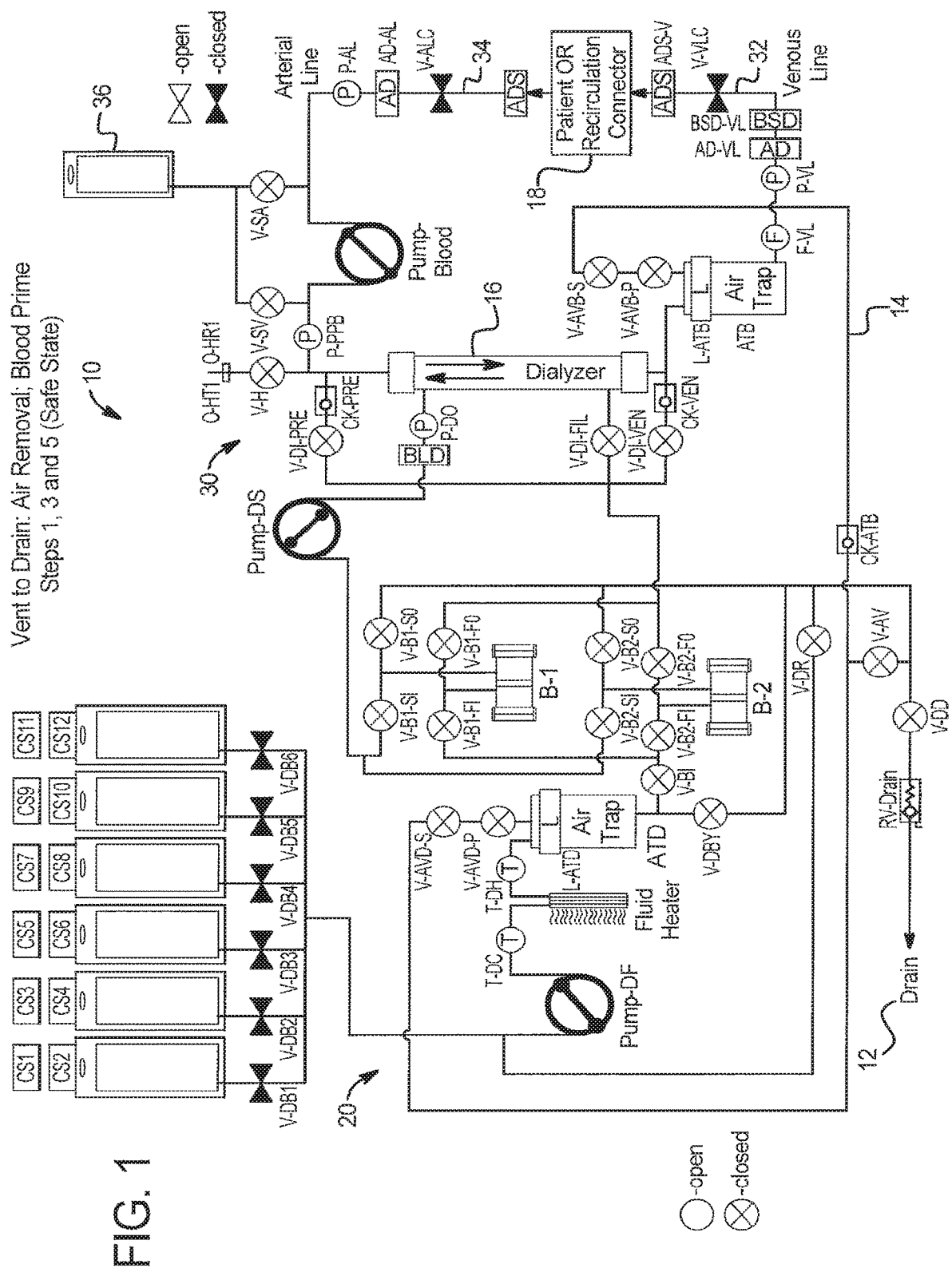
FIGS. 1 to 5 illustrate various steps for a method and corresponding system for venting air to drain.

The systems described herein include common components (unless otherwise stated), such as the following dialysate valves: V-AVD-P, which is a primary dialysate air vent valve; V-AVD-S, which is a secondary air vent valve; V-BI, which is a balance chamber or balance tube inlet valve; V-B1-FI, which is a balance chamber 1 fresh inlet valve; V-B1-FO, which is a balance 1 fresh outlet valve; V-B1-SI, which is a balance chamber 1 spent inlet valve; V-B1-SO, which is a balance chamber 1 spent outlet valve; V-B2-FI, which is a balance chamber 2 fresh inlet valve; V-B2-FO, which is a balance chamber 2 fresh outlet valve; V-DD, which is a dialysate drain valve; V-DR, which is a dialysate recirculation valve; V-DBY, which is a dialyzer bypass valve; V-DI-PRE, which is a dialysate/infusate predilution hemofiltration or hemodialfiltration valve; V-DI-VEN, which is a dialysate/infusate postdilution hemofiltration or hemodialfiltration valve; V-DI-FIL, which is a dialysate/infusate inlet to the filter, and V-AV, which is an airline vent valve.

Common blood valves (unless otherwise stated) include V-AVB-P, which is a primary blood vent valve; V-AVB-S, which is a secondary blood vent valve; V-SA, which is a saline to arterial side of blood circuit valve; V-SV, which is a saline to venous side of blood circuit valve; and V-H, which is a heparin valve.

The above valves are all volcano or cassette type valves in one embodiment (pneumatically or electromechanically actuated). The following valves can instead be pinch valves or clamps: V-DB1 through V-DB6, which open and close supply lines to solution bags 1 to 6, respectively; V-ALC, which is an arterial Line clamp (fail safe); and V-VLC, which is a venous line clamp (fail safe).

The systems each include temperature sensors, such as: T-DC, which is a dialysis solution preheat temperature sensor; and T-DH, which is a dialysis solution heated temperature. The systems each include pressure sensors, such as: P-DO, which senses a pressure of fluid leaving the dialyzer or filter; P-AL, which is an arterial line pressure sensor; P-VL, which is a venous line pressure sensor; P-PPB, which is a post blood pump pressure sensor.

The systems each include optical sensors, such as: for balance chamber 1, O-B1-T1, transmitter 1 transmits to O-B1-R1, receiver 1 for end of travel; O-B1-T2, transmitter 2 transmits to O-B1-R2, receiver 2 for end of travel; O-B1-T3, transmitter 3 transmits to O-B1-R3, receiver 3 for end of travel; O-B1-T4, transmitter 4 transmits to O-B1-R4, receiver 4 for end of travel. Balance chamber 2 has the same set of end of travel optical sensors. O-HT1 is a heparin transmitter that transmits to O-HR1, heparin receiver to look for heparin instead of blood.

The systems each include other sensors, such as: CS 1 to 12, which are capacitive sensors for sensing the presence and/or orientation of the solution bags. AD-AL, which is an arterial line, e.g., ultrasonic, air detector. AD-VL, which is a venous line, e.g., ultrasonic, air detector. AD-HL, which is a heparin line, e.g., ultrasonic, air detector. BSD-VL, which is a venous line blood/saline, e.g., optical, detector. L-ATD, which is a dialysate air trap level sensor. L-ATB, which is a blood air trap level sensor. BLD, which is an e.g., optical, blood leak detector. ADS-A, which is an arterial line access disconnection sensor. ADS-V, which is a venous line access disconnection sensor.

The systems also include a drain relief valve RV-Drain and check valves CK-ATB for blood air trap, CK-PRE for prefilter infusate and CK-VEN for venous infusate.

The systems also include a filter, F-VL, which is a venous line macro-aggregate filter and other components such as ATD, which is a dialysate air trap and ATB, which is an air trap for blood.

The above valves and sensing areas for the above sensors can be placed in one or more disposable pumping cassette. For example, the systems can employ dedicated blood and dialysate cassettes with integrated air traps. Suitable configurations for cassettes with air traps are disclosed in co-pending patent application Ser. No. 11/865,577, entitled "Dialysis Systems Having Air Traps With Internal Structures To Enhance Air Removal"; Ser. No. 11/865,583, entitled "Dialysis Systems Having Air Separation Chambers With Internal Structures To Enhance Air Removal"; Ser. No. 11/865,552, entitled "Dialysis System Having Air Separation Chambers With Internal Structures To Enhance Air Removal"; and 60/976,731, entitled "Fluid And Air Handling In Dialysis Circuit Air Removal System", each filed on Oct. 1, 2007, assigned to the eventual assignee of the present disclosure, the entire contents of each of which are incorporated expressly herein by reference.

I. Vent to Drain

Referring now to the drawings and in particular to FIGS. 1 to 5, in one primary embodiment a dialysis system 10 and corresponding method vents air to drain. System 10 can accomplish at least two tasks with the vent to drain option: (i) venting air that accumulates in an air trap ATD (air trap for dialysate) or ATB (air trap for blood) during prime or throughout the course of a therapy and (ii) purging extracorporeal circuit priming solution, e.g., saline, to drain (as opposed to returning to the solution to the patient).

Vent to Drain—Purging Air that Accumulates During Therapy

The air purging method of system 10 determines in one embodiment when it is necessary to remove air from the air trap, e.g., via an automatic level sensor L-ATD or L-ATB associated with air trap ATD and ATB, respectively, or via operator intervention. System 10 begins the air removal process by establishing an appropriate flow path from air trap ATD or ATB. The flow path from air trap ATD to drain 12 will be via dialysate circuit 20. The flow path from air trap ATB to drain 12 will be via blood circuit 30. Once the relevant flow path is open, system 10 displaces air from the air trap ATD or ATB, generating a pressure in the air trap that is higher than the pressure of drain 12. System 10 continues to displace air from the air trap ATD or ATB until automatic level sensor L-ATD or L-ATB, respectively, senses that it is no longer necessary to do so. Or, an operator visually determines that enough air has been removed from system 10.

One example of purging air from blood circuit 30 to drain 12 is illustrated in FIG. 1. Here the extracorporeal circuit level detector L-ATB detects a low fluid level. System 10 stops blood pump (PUMP-Blood) and dialysis solution pumps (PUMP-DF, PUMP-DS). System 10 closes venous patient line clamp V-VLC, saline valves V-SV, V-SA, heparin valve V-H, and extracorporeal air vent valves V-AVB-S, V-AVB-P in extracorporeal circuit 30. System 10 opens air vent valve V-AV and drain valve V-DD near drain 12.

System 10 then begins running PUMP-Blood clockwise, while metering air through the air vent valves V-AVB-S and V-AVB-P. Air vent valves V-AVB-S and V-AVB-P alternate in a chamber-lock type manner First, vent valve V-AVB-P is opened allowing air to pressurize the line up to vent valve V-AVB-S. Then, the valve states are reversed, allowing pressurized air trapped between the vent valves V-AVB-S and V-AVB-P to be released to drain 12 via air vent line 14. One of the vent valves is thus closed at all times, and the valves alternate at a rate related to the rate of PUMP-Blood.

The extracorporeal circuit level detector L-ATB may be used in combination with a blood leak detector BLD (see FIG. 5) to ensure that the blood level does not fall too low and to detect when the blood level has overfilled blood air trap ATB. When blood leak detector BLD detects an overfill, system 10 stops PUMP-Blood and closes extracorporeal air vent valves V-AVB-S and V-AVB-P, closes air vent valve V-AV, and closes drain valve V-DD. System 10 then opens venous patient line clamp V-VLC and saline valves V-SV, V-SA or heparin valve V-H if appropriate and restarts PUMP-Blood to push an appropriate amount of blood from air trap ATB to the patient, lowering the level in the air trap, and allowing fluid in vent line 14 sensed at BLD to fall back into blood from air trap ATB. Dialysis solution pumps DF and DS are also run at the same rates they were running before the air vent to dialyze blood that is being pushed through dialyzer 16 during the level lowering process within air trap ATB.

Vent to Drain—Purging Extracorporeal Priming Solution to Drain

System 10 begins a blood prime process after extracorporeal circuit 30 has been primed with priming fluid (saline, heparin, dialysis solution etc.). For blood prime, system 10 assures that the patient has been connected to the system or accessed. First, system 10 communicates circuit 30 with patient 18 flow path. System 10 then flows blood from patient 18, through the circuit 30, including air trap ATB, to displace priming fluid out of system 10 to the fluid drain 12, until the extracorporeal circuit is sufficiently primed with blood, e.g., using a blood detector BLD and/or flow sensing and/or a recorded number of pump rotations sufficient to completely remove priming fluid and/or a total time spent pumping sufficient to completely purge circuit 30 of priming fluid.

FIGS. 1 to 4 illustrate in detail how system 10 performs blood prime venting. In FIG. 1, system 10 performs a first step in which it is in a safe state following extracorporeal circuit prime with all valves and patient line clamps closed and all pumps stopped.

Figure 2:
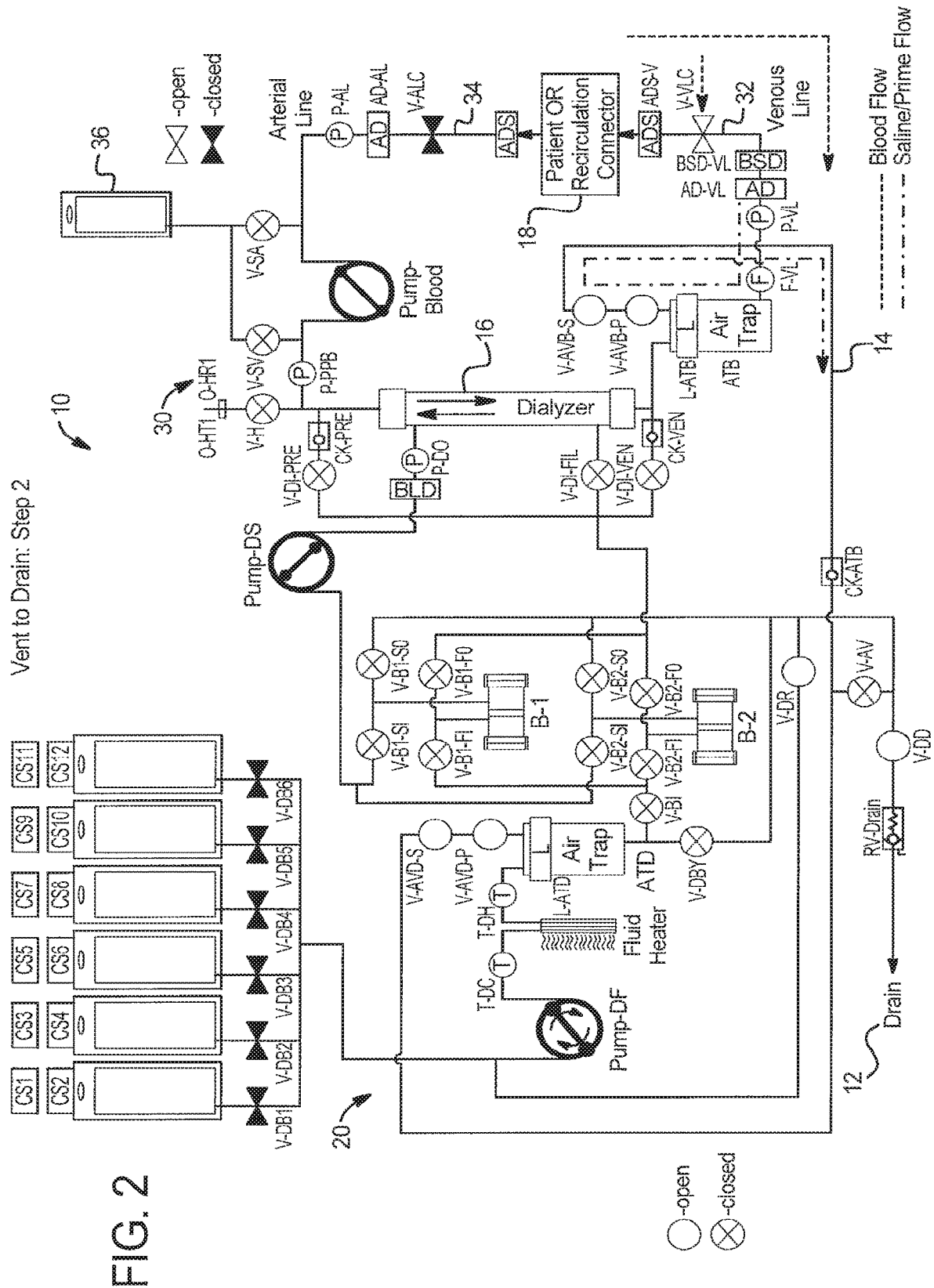

At step 2 in FIG. 2: (a) an operator establishes vascular access with a venous patient line 32 of blood circuit 30; (b) the operator establishes vascular access with the arterial patient line 34 of blood circuit 30; (c) system 10 prepares for blood prime by opening extracorporeal circuit air vent valves V-AVB-S and V-AVB-P, dialysate circuit air vent valves V-AVD-S and V-AVD-P, and drain valves V-DD and V-DR; (d) system 10 runs fresh dialysate pump DF in the clockwise direction as shown in FIG. 2 until the blood saline detector BSD-VL detects blood. System 10 can also run fresh dialysate pump DF longer, so blood moves beyond the blood saline detector, e.g., using a total number pump strokes as the indicator to finally stop dialysate pump DF. This operation pulls blood from patient 18, through venous or return line 32, to blood saline detector BSD-VL, displacing priming fluid in venous line 32 with the patient's blood. Negative pressure is applied by priming fluid being pulled through air vent line 14 and blood air trap ATB. Any air is pushed to drain via open valve V-DD.

Figure 12:
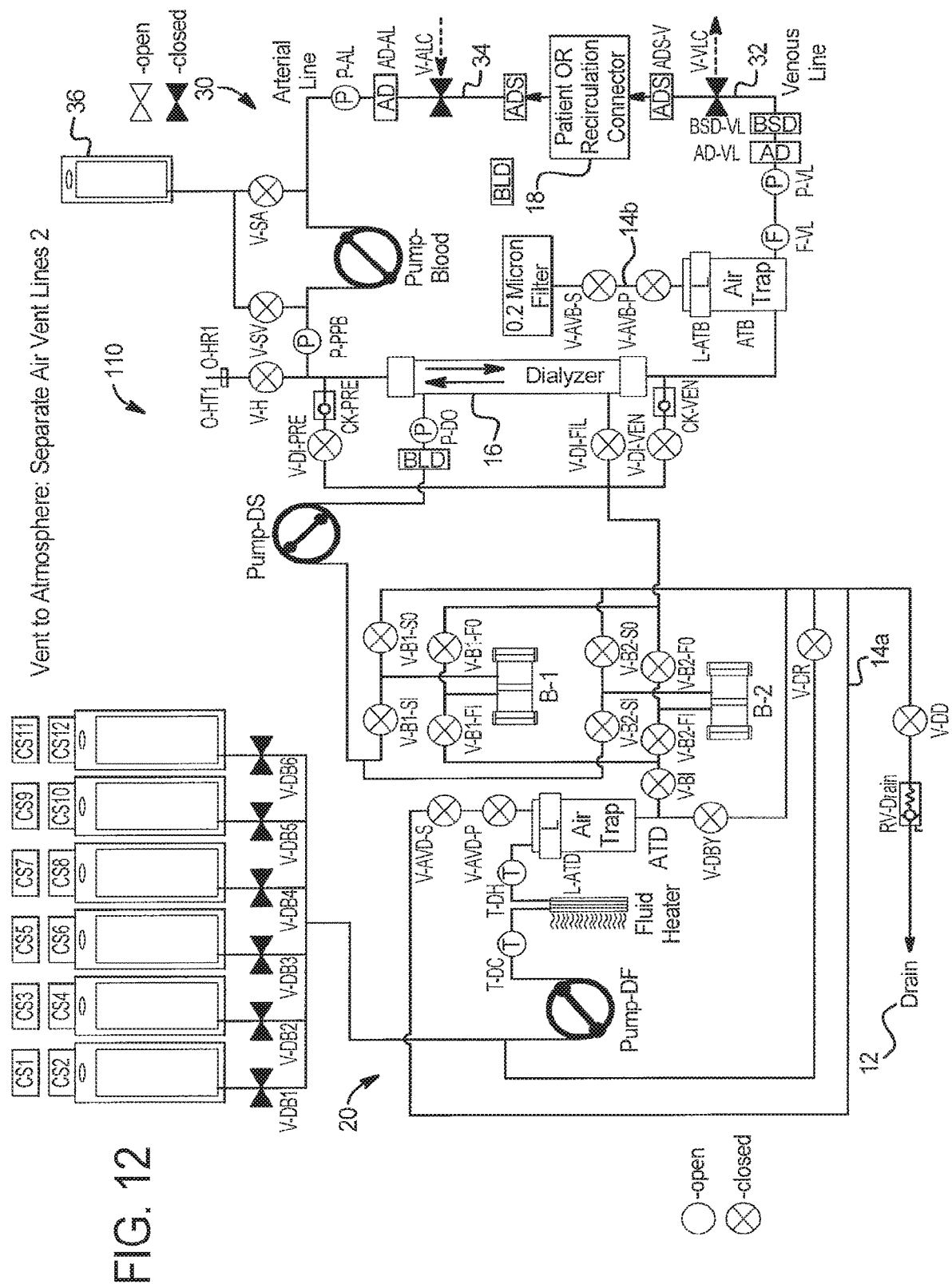

At step 3 in FIG. 12, system 10 returns to a safe state by closing all blood and dialysate valves and patient line clamps and stopping all pumps.

Figure 3:
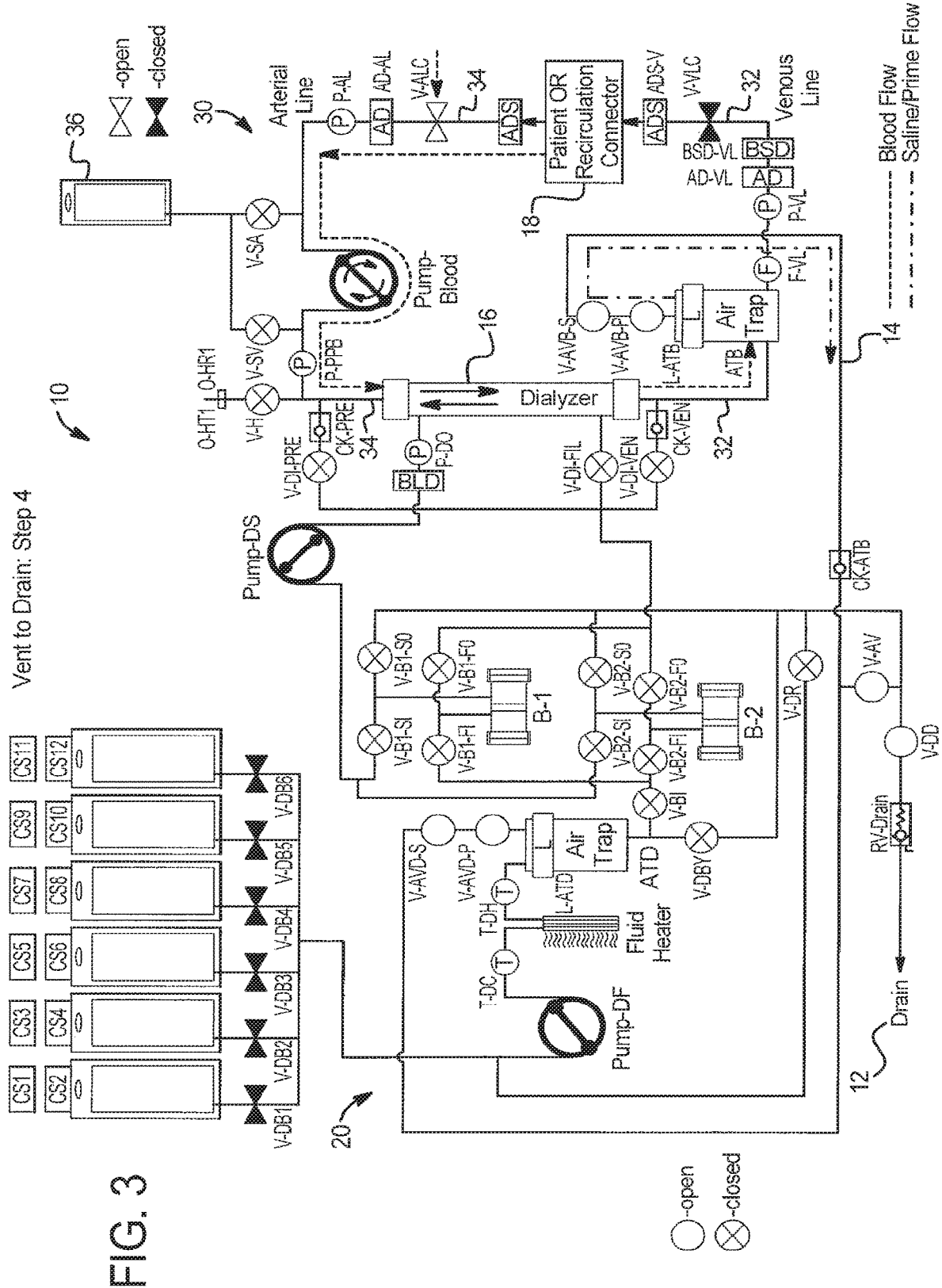

At step 4 in FIG. 3, system 10 prepares for completion of blood prime by opening extracorporeal circuit air vent valves V-AVB-S and V-AVB-P, dialysate circuit air vent valves V-AVD-S and V-AVD-P, arterial patient line clamp V-ALC, and drain valve V-DD. System 10 starts PUMP-Blood in the clockwise direction as shown in FIG. 3 and runs the pump for a specific number of pump strokes or a specific period of time until blood travels from patient 18, through arterial line 34, dialyzer 16, and a portion of venous line 32 to blood air trap ATB. System 10 can also run PUMP-Blood longer so blood moves into the air trap ATB, provided system 10 can verify that blood does not leave blood air trap ATB during the rest of the priming process.

At step 5 in FIG. 1, system 10 returns to a safe state by closing all valves and patient line clamps and stopping all pumps. All saline has been removed from blood circuit 30 except perhaps for a small amount between blood air trap ATB and blood saline detector BSD-VL. Again, any air is pushed to drain via valve V-DD.

Vent to Drain—Alternative Vent Valving

Figure 4:
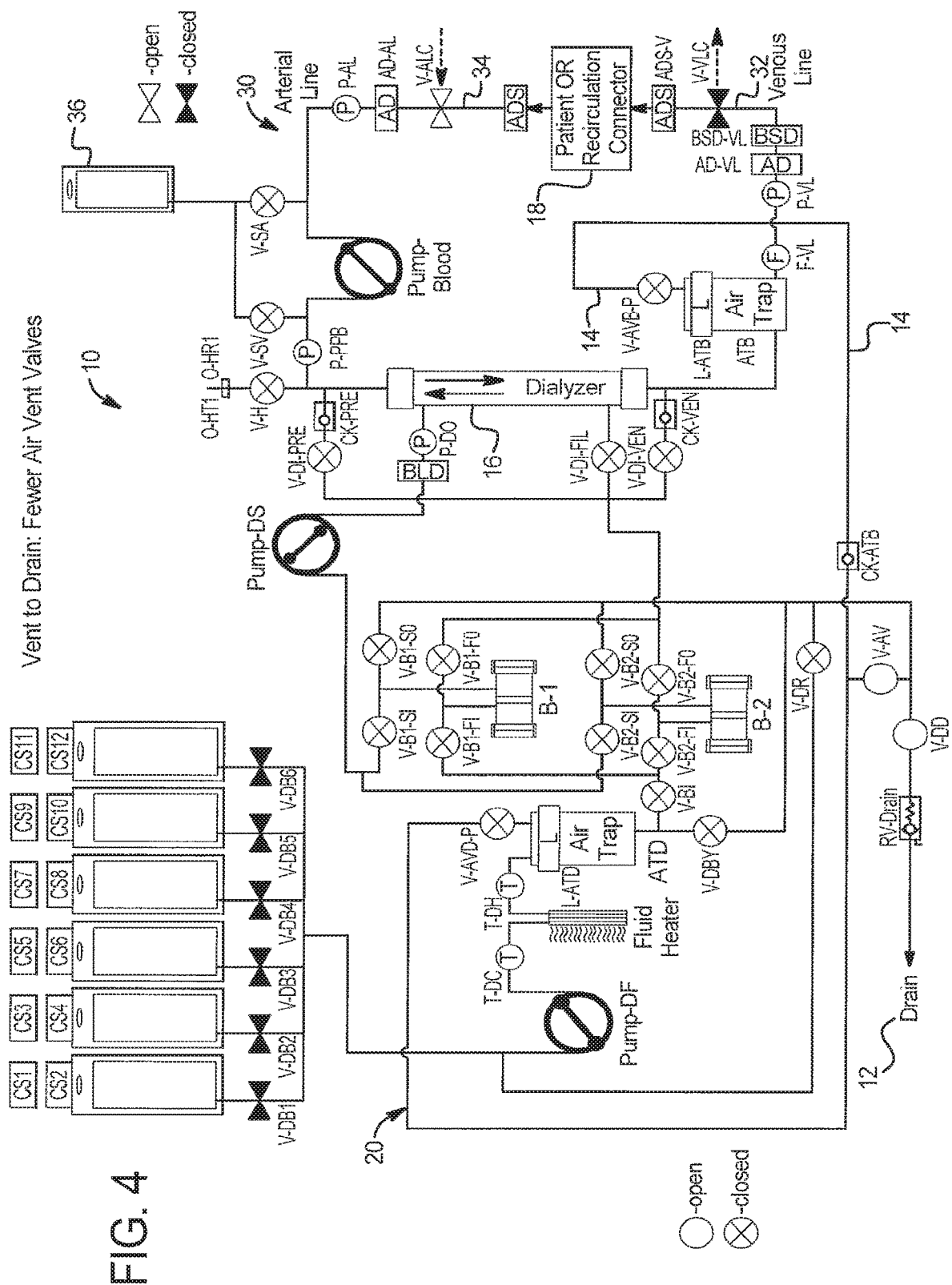

Referring now to FIG. 4, secondary air vent valves V-AVD-S and V-AVB-S for the dialysate circuit 20 and extracorporeal circuit 30, respectively, have been removed to reduce hardware. The vent to drain and priming fluid to drain sequences above may be performed using the reduced vent valve arrangement of FIG. 4. To increase safety, a blood leak detector BLD may be added to vent line 14 upstream of the singly used air vent valves V-AVD-P and V-AVB-P. Since system 10 is closed to drain, it may be possible to eliminate both the primary and secondary vent valves.

Vent to Drain—Extra Blood Detector

Figure 5:
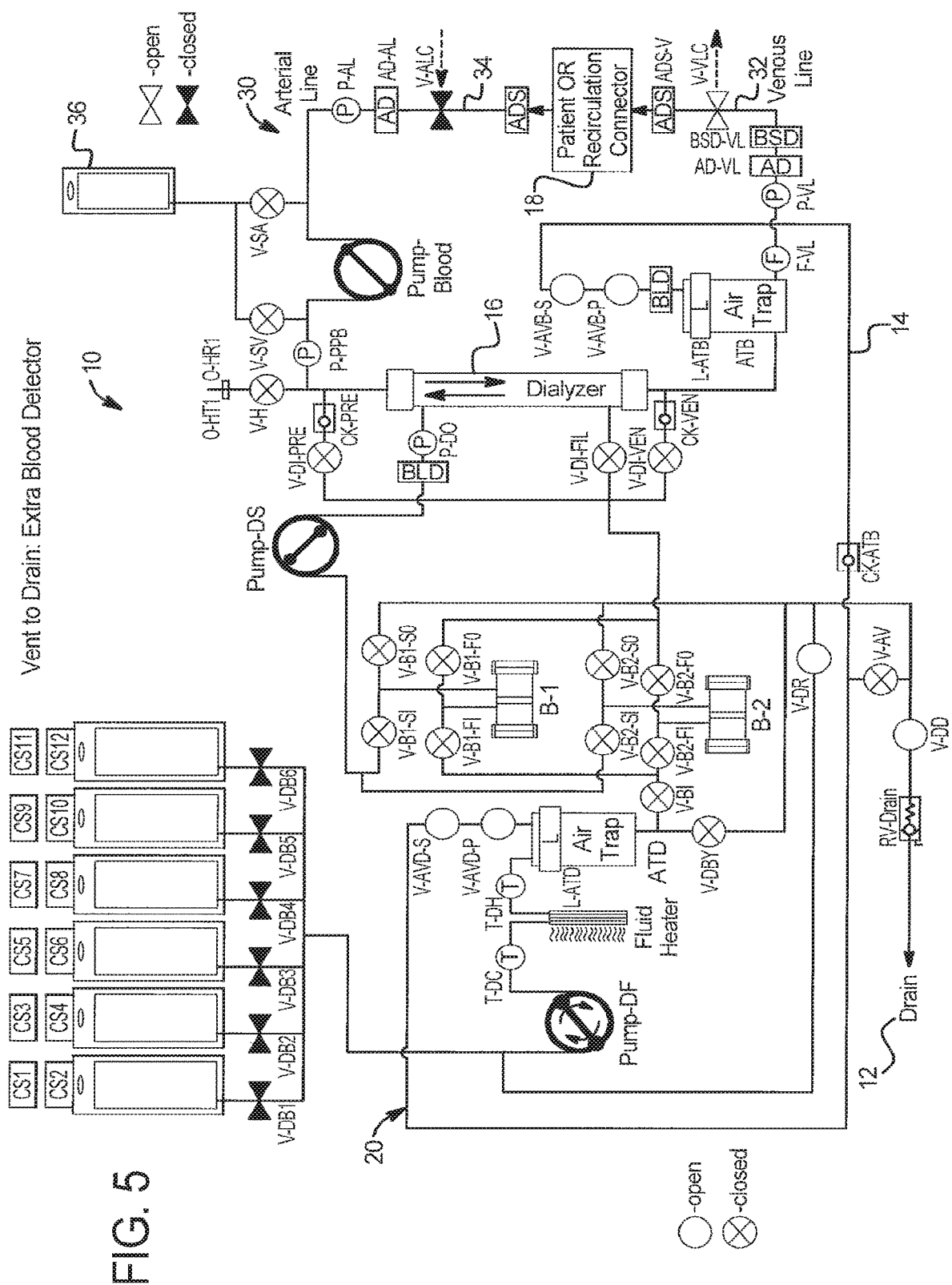

Referring now to FIG. 5, to prime the extracorporeal circuit 30 to a greater extent, a blood detector BLD can be placed in the post-air trap air vent line, between trap ATB and vent valve V-AVB-P or alternatively between valves V-AVB-P and V-AVB-S. In FIG. 5, dialysate pump DF is shown pulling saline, as described shown in FIG. 2, in turn pulling blood to the added detector BLD. Blood could be drawn alternatively to detector BLD via PUMP-Blood via the process of FIG. 3. An advantage in either case is that more of the air trap priming volume or saline is sent via drain line 14 to drain 12.

Vent to Drain—Fluid Use Efficiency

It is also possible in the vent to drain system 10 embodiments to maximize fluid use efficiently by pumping dialysis solution to prime the extracorporeal circuit. Here, a suitable path of valves is opened to allow fresh dialysate pump DF to pump fresh dialysate into dialyzer 16, and through the hollow fiber membranes of the dialyzer, into extracorporeal circuit 30. In this manner, system 10 can remove air from circuit 30 to drain using dialysate instead of requiring an extra priming fluid, such as saline. The dialysate can then be replaced with blood as shown above, so that the dialysate volume is not delivered to the patient.

II. Vent to Atmosphere

In another primary embodiment shown in FIGS. 6 to 12, the system 10 vents air to atmosphere. System 10 can accomplish at least two tasks using the vent to atmosphere option: (i) venting air that accumulates in the blood air trap during prime or throughout the course of a therapy and (ii) purging the extracorporeal circuit priming solution to drain (as opposed to returning the priming solution to the patient).

Vent to Atmosphere—Purging Air that Accumulates During Therapy

In the vent to atmosphere embodiment, system 110 determines when it is necessary to remove air from the extracorporeal or dialysate side air traps ATD and ATB via automatic level sensors L-ATD and L-ATB and/or operator intervention as discussed above. System 110 begins the air removal process by establishing an appropriate flow path from the air trap ATD or ATB to atmosphere. Once the flow path is open, system 110 displaces air from the relevant air trap ATB, generating a higher than atmospheric pressure in the associated air trap and/or generating a lower than air trap pressure in the atmosphere, e.g., drawing a vacuum on the air trap. System 110 continues to displace air from the air trap until it is no longer necessary to do so (as determined by automatic level sensors L-ATD or L-ATB and/or via operator intervention.

Figure 6:
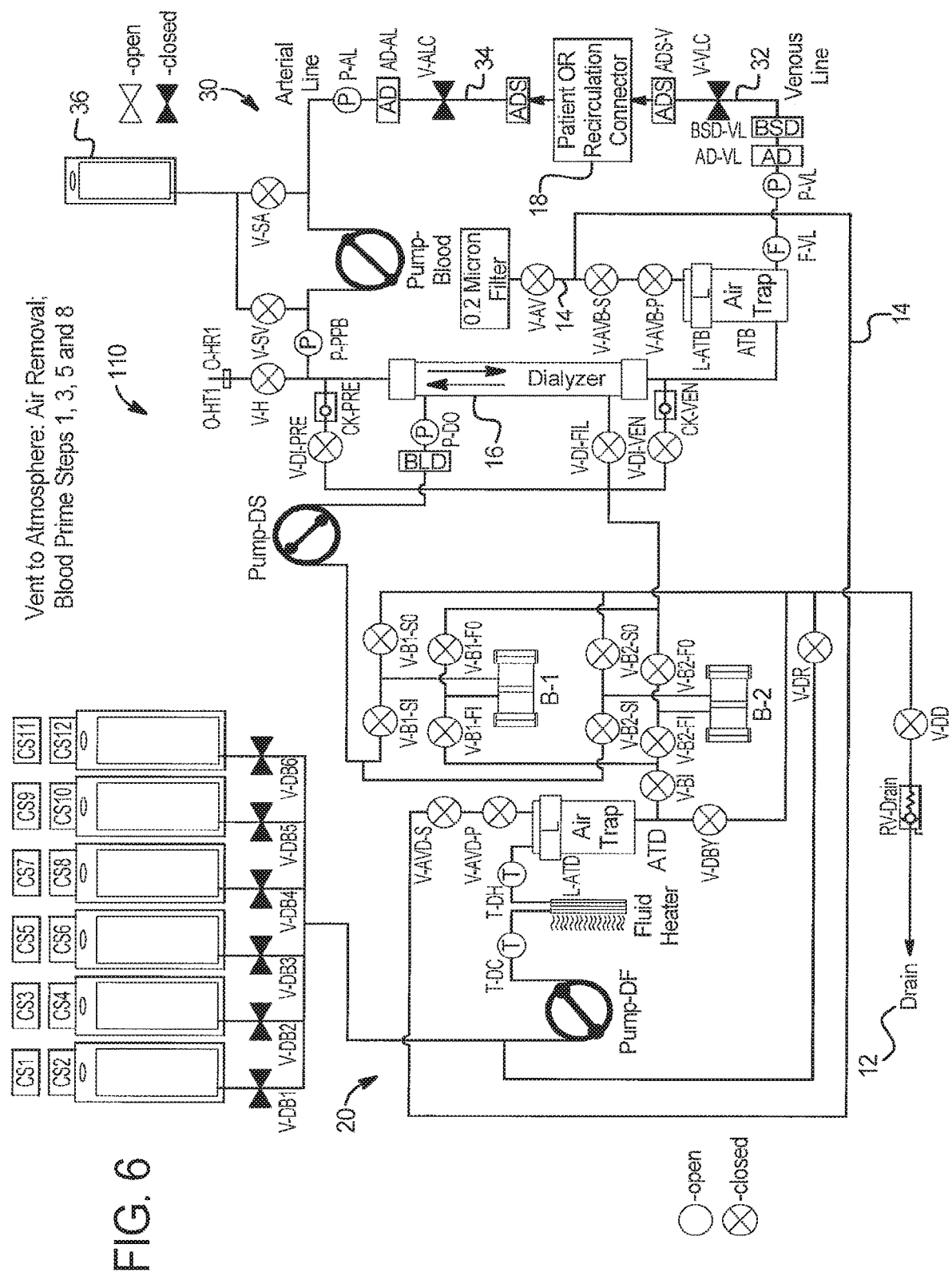
FIGS. 6 to 12 illustrate various steps for a method and corresponding system for venting air to atmosphere.

FIG. 6 illustrates an embodiment of system 110 in which venting to atmosphere can be accomplished. System 110 differs form system 10 primarily in that system 110 has connected drain vent valve V-AV to atmosphere through a 0.2 micron filter instead of connecting it to the drain lines as in system 10. All air is vented through dialysate vent valve V-AV to atmosphere through this filter.

In one sequence, the extracorporeal circuit level detector L-ATB detects a low fluid level. System 110 stops PUMP-Blood and dialysis solution pumps DF and DS. System 110 closes venous patient line clamp V-VLC, saline valves V-SV and V-SA, heparin valve V-H, and extracorporeal air vent valves V-AVB-S, V-AVB-P and opens saline valve V-SA. System 110 then slowly runs PUMP-Blood clockwise (as oriented in FIG. 6), drawing in blood while metering air through the air vent valves V-AVB-S and V-AVB-P and through open valve V-AV and out the 0.2 micron filter. One of the vent valves is closed at all times as described above to ensure that no outside air contacts blood.

The extracorporeal circuit level detector L-ATB may be used in combination with a blood leak detector BLD (see FIG. 5) to ensure that the blood level does not fall too low and to detect when the blood level has overfilled blood air trap ATB. When blood leak detector BLD detects an overfill, system 110 closes extracorporeal air vent valves V-AVB-S and V-AVB-P, opens venous patient line clamp V-VLC and saline valves V-SV, V-SA or heparin valve V-H if appropriate and restarts dialysis solution pumps DF and DS and Pump-Blood at the same rates that they were running before the venting of air through trap ATB, vent valve V-AV, and 0.2 micron filter.

Vent to Atmosphere—Purging Extracorporeal Priming Solution to Drain

System 110 begins a blood prime process after extracorporeal circuit 30 has been primed with priming fluid (saline, heparin, dialysis solution etc.). For blood prime, system 110 assures that the patient has been connected to the system or accessed. First, system 110 communicates circuit 30 with patient 18. System 110 then flows blood from patient 18 through the circuit 30, including air trap ATB to displace priming fluid out of system 110 to the fluid drain 12 until the extracorporeal circuit is sufficiently primed with blood, e.g., using a blood detector BLD and/or flow sensing and/or a recorded number of pump rotations sufficient to completely remove priming fluid and/or a total time spent pumping sufficient to purge circuit 30 of priming fluid.

FIGS. 6 to 10 illustrate in detail how system 110 accomplishes blood prime venting to atmosphere.

In step 1 at FIG. 6, system 110 is in a safe state following extracorporeal circuit prime with all valves and patient line clamps closed and all pumps stopped.

Figure 7:
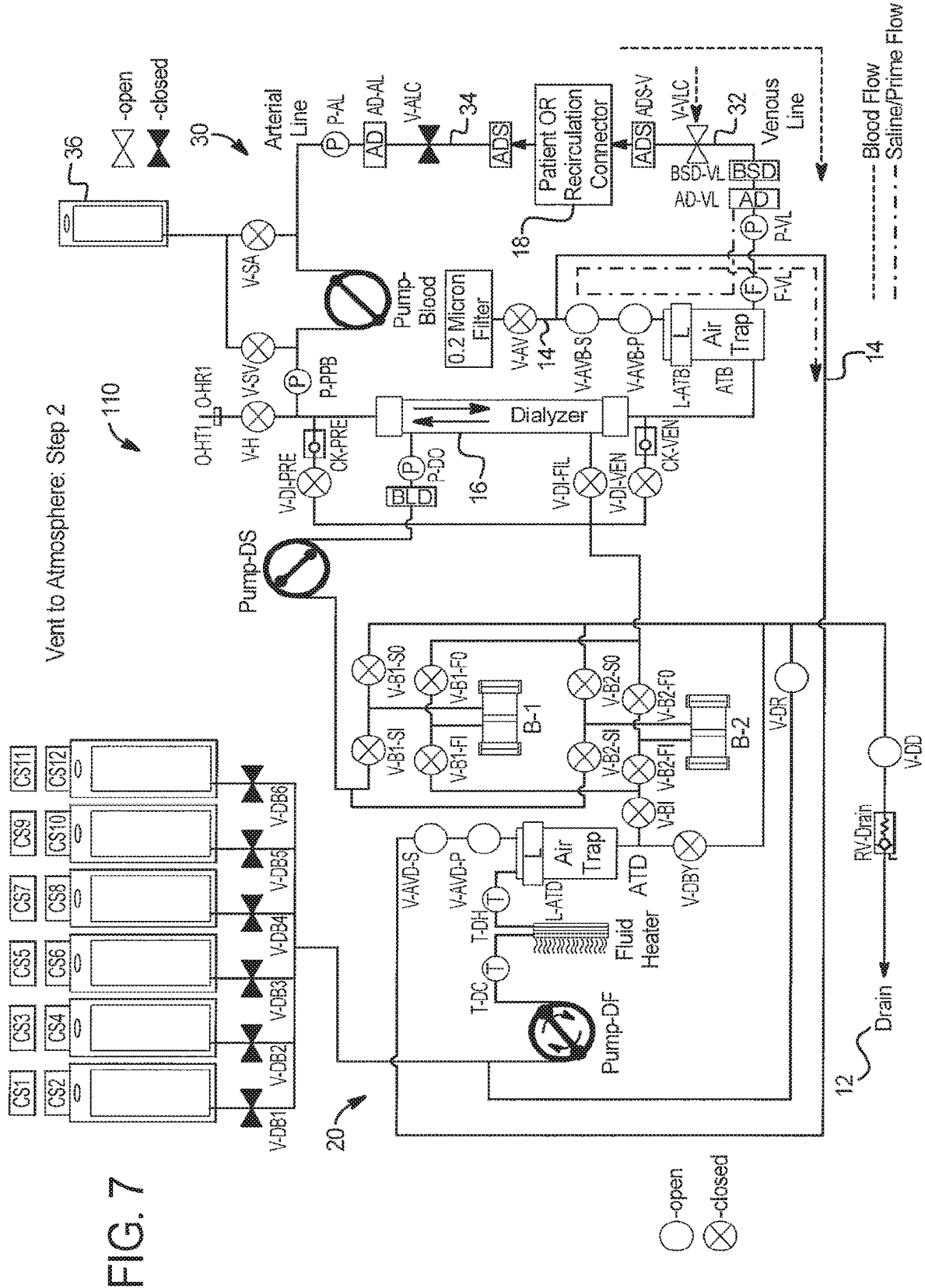

In step 2 at FIG. 7: (a) an operator establishes vascular access with the venous patient line 32; (b) system 110 prepares for blood prime by opening extracorporeal circuit air vent valves V-AVB-S and V-AVB-P, dialysate circuit air vent valves V-AVD-S and V-AVD-P, and drain valves V-DD and V-DR; and (c) system 110 runs fresh dialysate pump PUMP-DF in the clockwise direction as seen in FIG. 7 and until the blood saline detector BSD-VL detects blood. It is also be possible to run the fresh dialysate pump DF longer, so blood moves beyond the blood saline detector BSD-VL using total pump strokes as the indicator to stop, for example.

In step 3 at FIG. 6, system 110: (a) returns to safe state by closing all valves and patient line clamps and stopping all pumps; and (b) the operator establishes vascular access with the arterial patient line 34.

Figure 8:
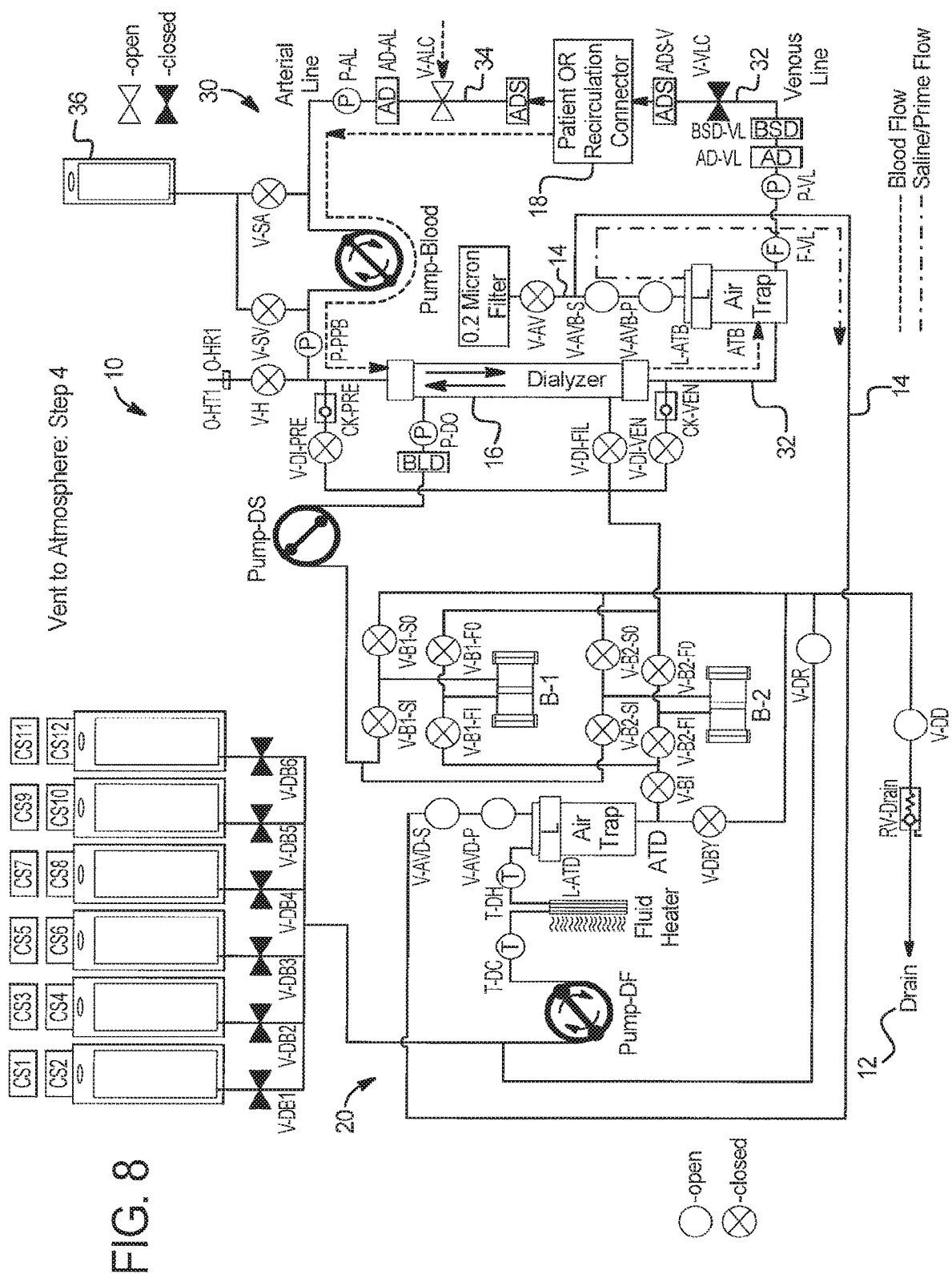

In step 4 at FIG. 8: (a) system 110 prepares for blood prime by opening extracorporeal circuit air vent valves V-AVB-S and V-AVB-P, dialysate circuit air vent valves V-AVD-S and V-AVD-P, and drain valves V-DD and V-DR; (b) system 110 runs PUMP-Blood in the clockwise direction, and the fresh dialysate pump DF in the clockwise direction as shown in FIG. 8 at the same flow rate for a specific number of pump strokes or period of time until blood flows through arterial line 34, dialyzer 16, and a portion of venous line 32 until reaching air trap ATB. Pressure sensor P-PPB can be used to indicate when one pump is running at a higher flow rate than the other. It is also possible to run the pumps longer, so blood moves into the air trap, provided that system 110 can verify that blood never leaves the air trap during the rest of the priming process. A blood-saline-air detector can be installed between V-AVB-P and V-AVB-S to further optimize priming solution removal.

In step 5 at FIG. 6, system 110 returns to the safe state by closing all valves and patient line clamps and stopping all pumps.

Figure 9:
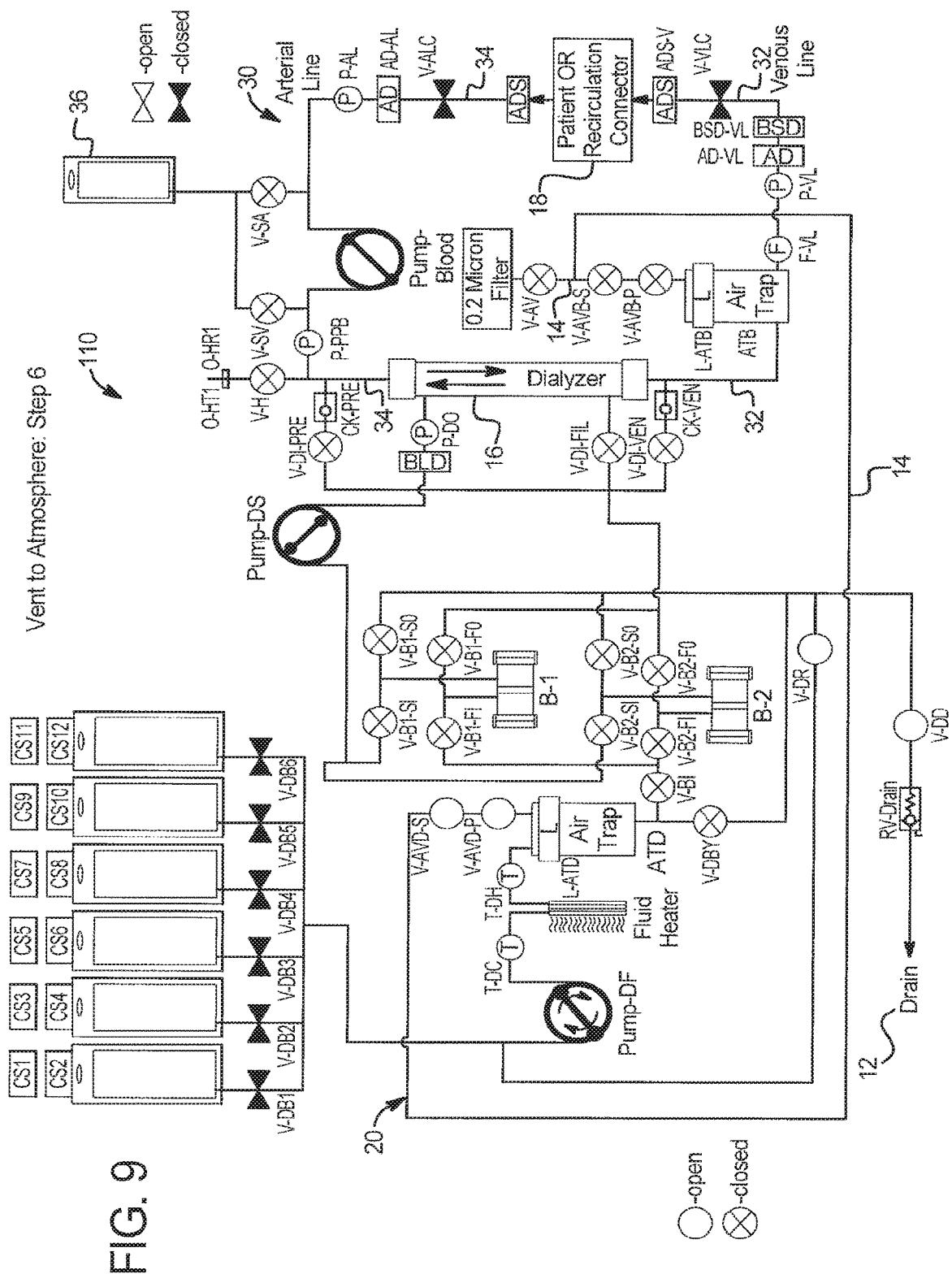

In step 6 at FIG. 9, system 110 prepares to clear the dialysate circuit side of the air vent by opening the air vent valve V-AV, dialysate circuit air vent valves V-AVD-S and V-AVD-P, and drain valves V-DD and V-DR.

Figure 10:
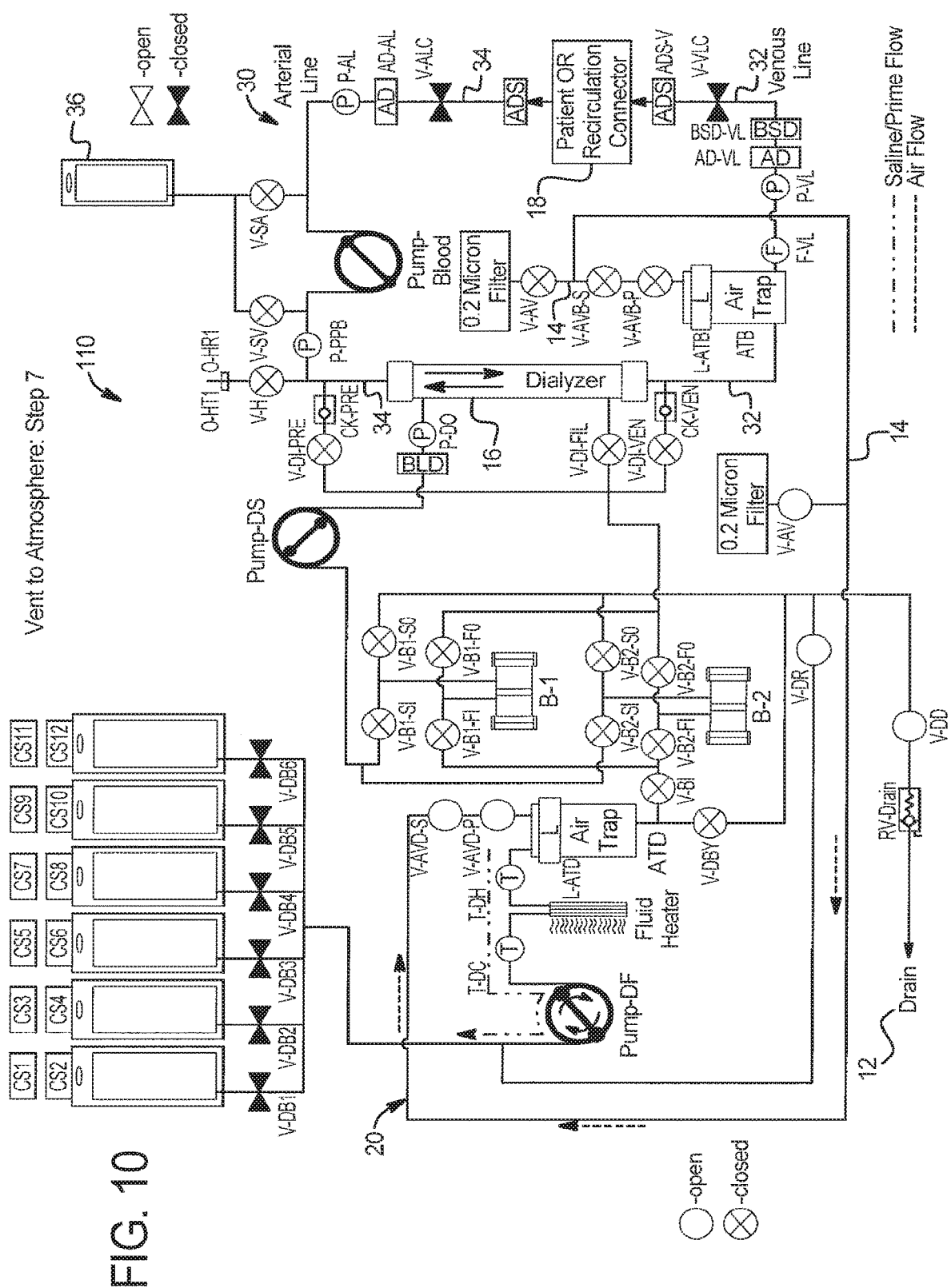

In step 7 at FIG. 10, system 110 runs the fresh dialysate pump L-ATB-DF in the clockwise direction, pumping fresh fluid from air trap ATB and pulling air into the trap via air vent line 14 and vent valves V-AVD-S and V-AVD-P until level detector L-ATD in the dialysate circuit air trap ATD indicates a certain level. System 110 can alternatively accomplish this step by running dialysate pump DF for a specific number of pump strokes or period of time until fluid is completely removed from the dialysate circuit air vent line 14.

In step 7 at FIG. 10, system 110 runs the fresh dialysate pump L-ATB-DF in the clockwise direction, pumping fresh fluid from line 14 and pulling air into the trap ATD via air vent line 14 and vent valves V-AVD-S and V-AVD-P until level detector L-ATD in the dialysate circuit air trap ATD indicates that there is no fluid in air trap ATD. System 110 can alternatively accomplish this step by running dialysate pump DF for a specific number of pump strokes or period of time until fluid is completely removed from the dialysate circuit air vent line 14.

In step 8 at FIG. 6, system 110 returns to safe state by closing all valves and patient line clamps and stopping all pumps.

During the therapy, if air gathers in the top of air trap ATB, valves V-AVB-P and V-AVB-S are alternately opened so that air is shuttled out of the air trap without allowing any blood to escape and vented through valve V-AV and the 0.2 micron vent filter.

Vent to Atmosphere—Alternative Vent Valving

Just like with FIG. 4 for venting to drain, system 110 can be modified to remove secondary air vent valve V-AVB-S from blood circuit 30 and V-AVD-S from dialysate circuit 20 to reduce hardware, which can also be performed by adding a blood leak detector BLD in vent line 14 upstream of the primary vent valves V-AVB-P and V-AVD-P to sense any blood that may enter vent line 14. Since venting is done to atmosphere, at least a primary vent valve should be provided at the blood and dialysate air traps ATB and ATD.

Vent to Atmosphere—Extra Drain/Air Vent Lines

Figure 11:
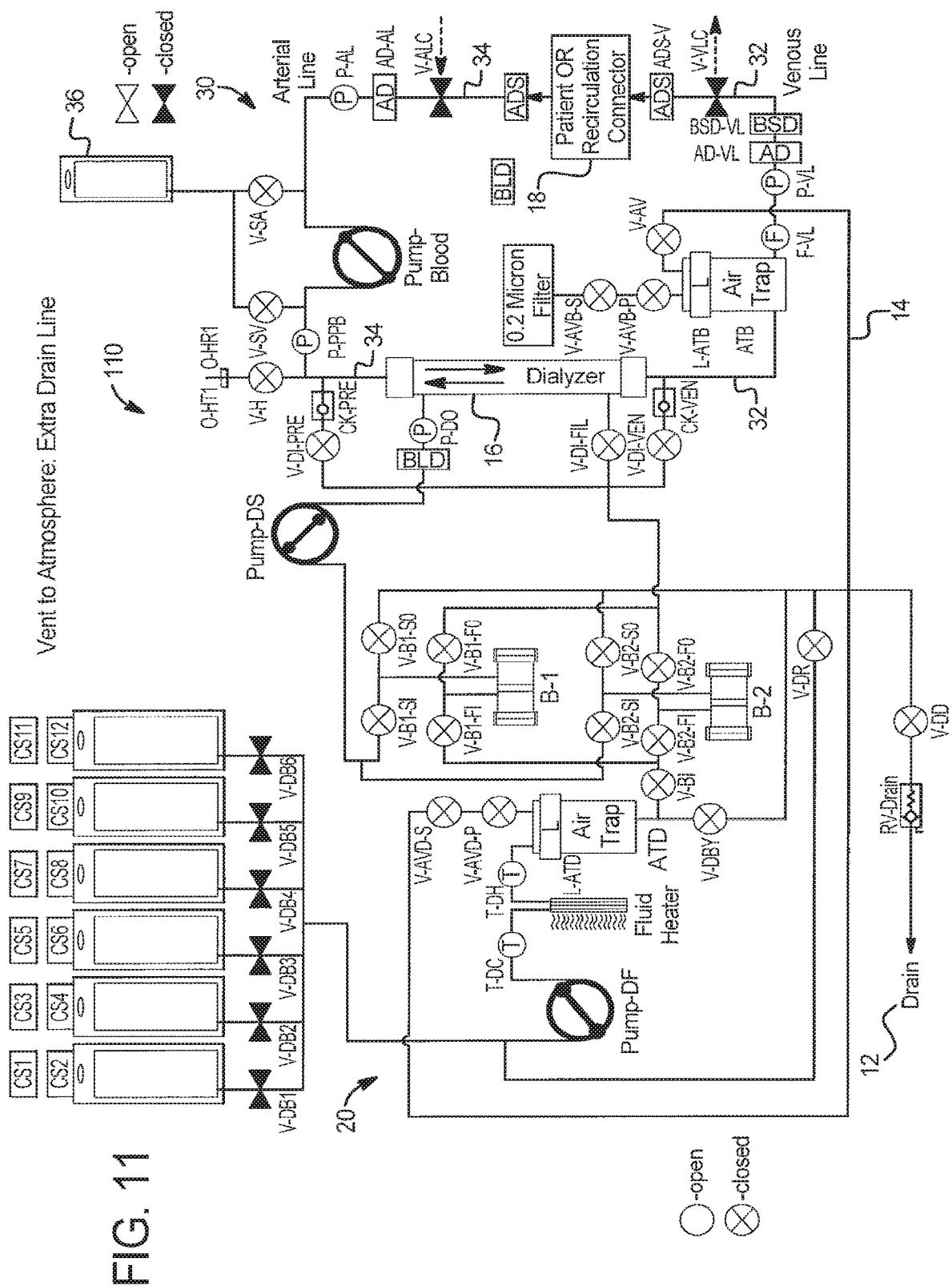

FIG. 11 illustrates that system 110 can alternatively connect air vent line 14 running from air traps ATB and ATD directly to drain line 12, similar to the vent to drain system 10. Unlike system 10, which provides an extra vent to drain valve V-AV for both air traps, system 110 uses vent valves V-AVD-S and V-AVD-P to control flow from dialysate air trap ATD to drain 12. Valve V-AC is provided as a vent valve for blood air trap ATB, which provides a second vent to atmosphere option using vent valves V-AVB-S and V-AVB-P and a 0.2 micron filter.

FIG. 12 illustrates that system 110 can alternatively have separate air vent lines for the dialysate and extracorporeal circuits, allowing the circuits to both vent at the same time. In FIG. 12, dialysate air vent line 14a runs to drain 12, while blood air trap ATB vents directly to atmosphere via vent line 14b, valves V-AVB-S And V-AVB-P and a 0.2 micron filter.

Vent to Atmosphere—Extra Blood Detector

In an alternative vent air to atmosphere embodiment, to prime the extracorporeal circuit to a greater extent, a blood detector BLD (see FIG. 5) can alternatively be placed in the post air-trap air vent line 14. An advantage here is that more of the air trap fluid priming volume can be replaced with blood before treatment.

Vent to Atmosphere—Alternative Method

Referring again to FIG. 6, in a further alternative embodiment, vent to atmosphere system 110 maximizes fluid use efficiency by pumping dialysis solution to prime the extracorporeal circuit 30. Here, a suitable path of valves is opened to allow fresh dialysate pump DF to pump fresh dialysate into dialyzer 16, and through the hollow fiber membranes of the dialyzer, into extracorporeal circuit 30. In this manner, system 110 can remove air from circuit 30 to drain using dialysate instead of requiring an extra priming fluid, such as saline. The dialysate can then be replaced with blood as discussed above, so that the dialysate volume is not delivered to the patient.

Vent to Atmosphere—Fluid Use Efficiency

It is also possible in the vent to atmosphere system 110 to use dialysis solution to prime extracorporeal circuit 30 as discussed above with vent to drain system 10.

III. Vent to Saline Bag

In a further alternative primary embodiment shown in FIGS. 13 to 18, system 210 vents to a bag such as a saline bag 36. Here again, system 210 can accomplish at least two tasks: (i) venting air that accumulates in air traps ATB and ATD during prime or throughout the course of a therapy and (ii) purging the extracorporeal circuit priming solution to saline bag 36 as opposed to returning the solution to patient 18.

Vent to Saline Bag—Purging Air that Accumulates During Therapy

System 210 determines when it is necessary to remove air from air trap ATB and ATD (via e.g., automatic level sensors L-ATB and L-ATD and/or operator intervention). System 210 begins the air removal process to by establishing an appropriate flow path from the air trap (extracorporeal ATB, dialysate ATD) to the saline bag 36. Once the flow path is open, system 210 displaces air from the air trap ATB or ATD by generating a higher than saline bag pressure in the air trap ATB or ATD and/or generating a lower than air trap pressure in the saline bag 36. System 210 continues to displace air from the air trap ATB or ATD until it is no longer necessary to do so, for example as determined by automatic level sensors L-ATB or L-ATD and/or operator intervention.

Figure 13:
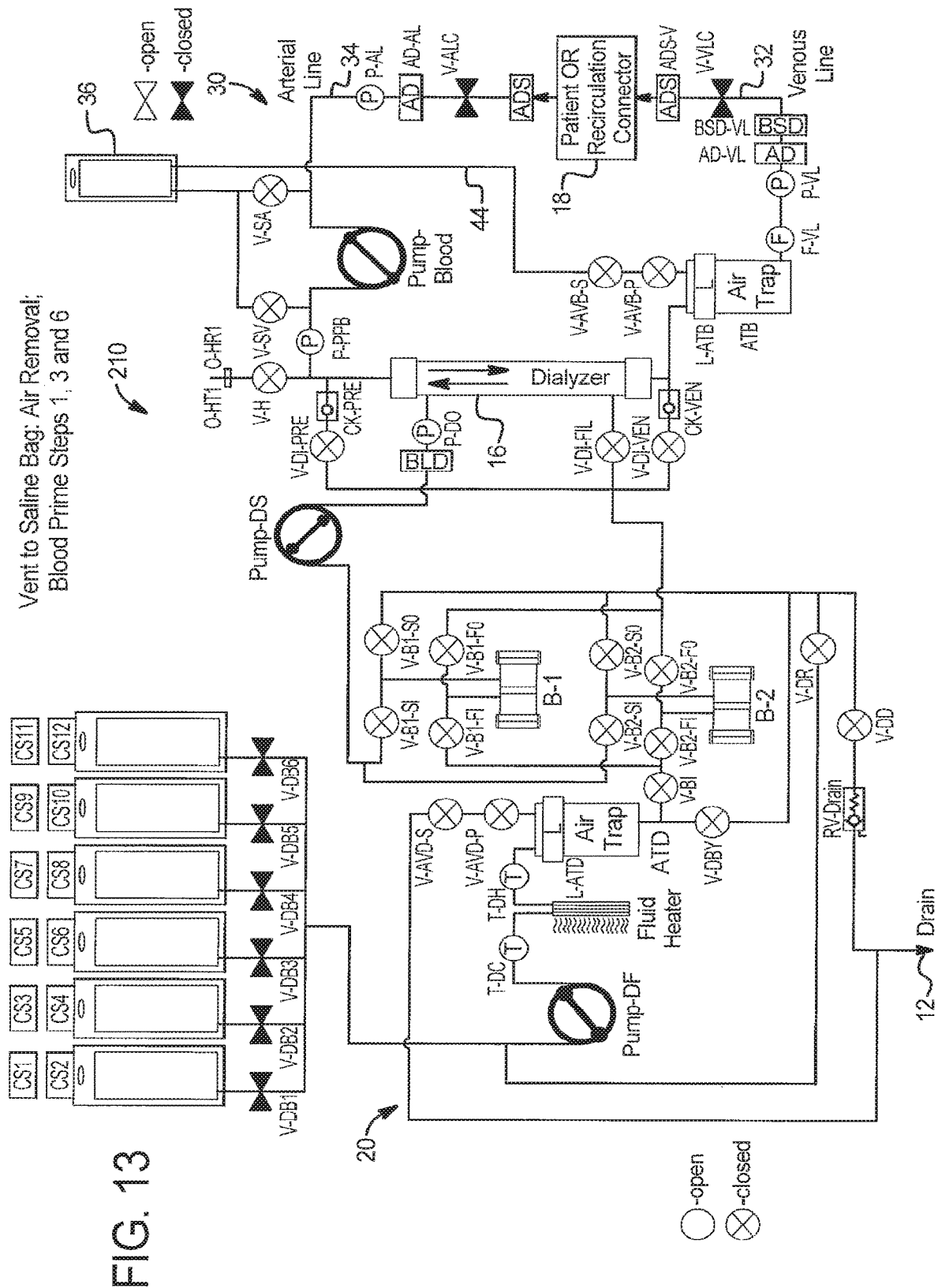
FIGS. 13 to 18 illustrate various steps for a method and corresponding system for venting air to a bag, such as a saline bag.

FIG. 13 illustrates system 210, which vents air to saline bag 36. When extracorporeal circuit level detector L-ATB detects a low fluid level of fluid within trap ATB, system 210 stops PUMP-Blood and dialysis solution pumps DF and DS. System 210 closes venous patient line clamp V-VLC, saline valves V-SV, V-SA, heparin valve V-H and extracorporeal air vent valves V-AVB-S and V-AVB-P.

System 210 then runs Pump-Blood clockwise, while metering air through the air vent valves V-AVB-S or V-AVB-P. Either valve V-AVB-S or V-AVB-P is closed at all times for safety. The valves alternate in a chamber lock manner, which can be cycled at a rate related to the blood pump rate. This action pushes air to saline bag 36.

The extracorporeal circuit level detector L-ATB may be used in combination with a blood leak detector BLD (see FIG. 5) to ensure that the blood level does not fall too low and to detect when the blood level has overfilled blood air trap ATB. When blood leak detector BLD detects an overfill, system 210 stops PUMP-Blood, closes extracorporeal air vent valves V-AVB-S and V-AVB-P, opens venous patient line clamp V-VLC and saline valves V-SV, V-SA or heparin valve (V-H) if appropriate; and runs Pump-Blood and dialysis solution pumps DS and DF at the same rates they were running before the air vent action. Such action pulls air saline from bag 36 into trap ATB, which pushes blood from the trap ATB.

Vent to Saline Bag—Purging Extracorporeal Priming Solution to Drain

The blood prime process of system 210 begins after the extracorporeal circuit has been primed with priming fluid (saline, heparin, dialysis solution etc.). Blood prime assumes that the patient's blood access has been connected to the system. First, system 210 establishes the appropriate flow paths accomplished with the illustrated (FIG. 13) system of valves and clamps. System 210 then flows blood from patient 18 through the appropriate flow path (which includes air trap ATB) to displace priming fluid saline bag 36 to other containers. System 210 then switches the flow path to continue to displace priming fluid until extracorporeal circuit 30 is sufficiently primed with blood. System 210 can determine if the blood prime is complete using a blood detector, flow sensing, or a recorded number pump rotations and/or a total time spent pumping. As with system 110, vent to bag system 210 does not need an extra vent valve V-AV provided with system 210. System 210 replaces vent line 14 with saline vent line 44.

FIGS. 13 to 16 illustrate in detail how blood prime venting to saline bag 36 or other bag can be accomplished.

In step 1 at FIG. 13, system 210 is placed in a safe state following extracorporeal circuit prime with all valves and patient line clamps closed and all pumps stopped.

Figure 14:
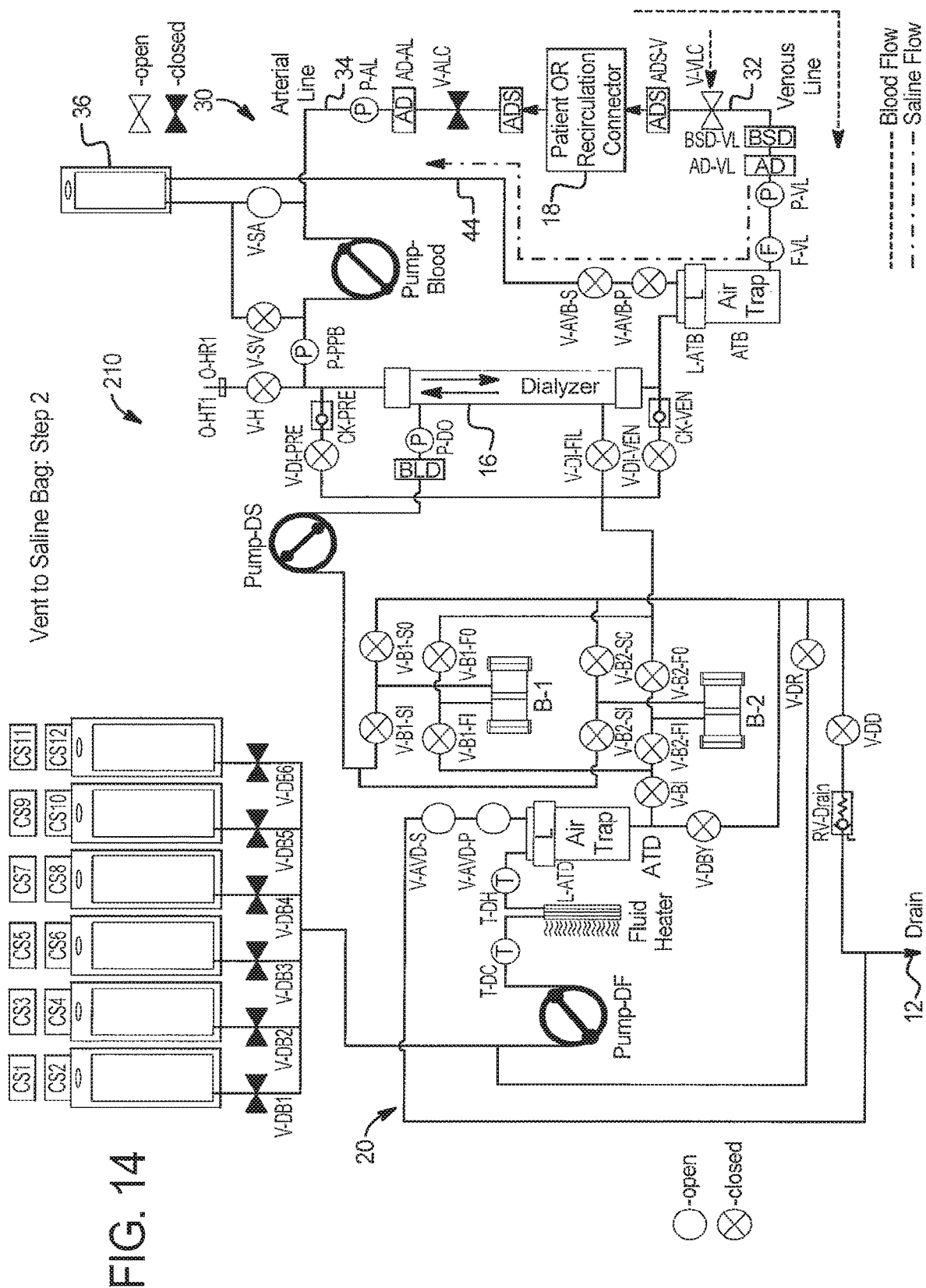
Figure 17:
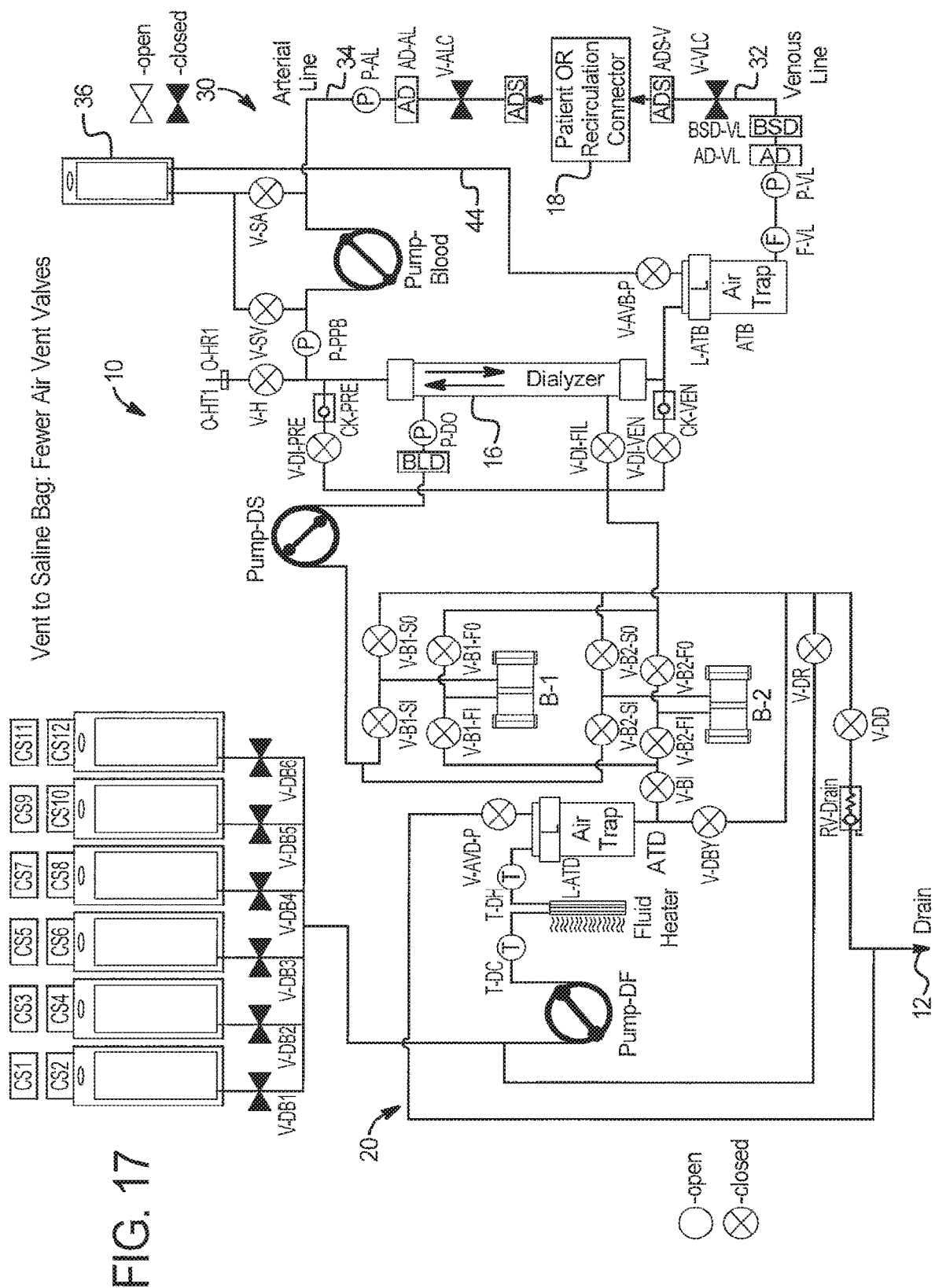

In step 2 at FIG. 14: (a) the operator establishes vascular access with the venous patient line 32; (b) the operator establishes vascular access with the arterial patient line 34; (c) system 210 prepares for blood prime by opening venous patient line clamp V-VLC and saline valve V-SA; and (d) system 210 runs PUMP-Blood in the counterclockwise direction as seen in FIG. 17, pumping blood from patient 18, through venous line 32 until the blood saline detector BSD-VL detects blood. System 210 can alternatively run the PUMP-Blood longer so blood moves beyond the blood saline detector BSD, e.g., using total pump strokes as the indicator to stop.

In step 3 at FIG. 13, system 210 returns to the safe state by closing all valves and patient line clamps and stopping all pumps.

Figure 15:
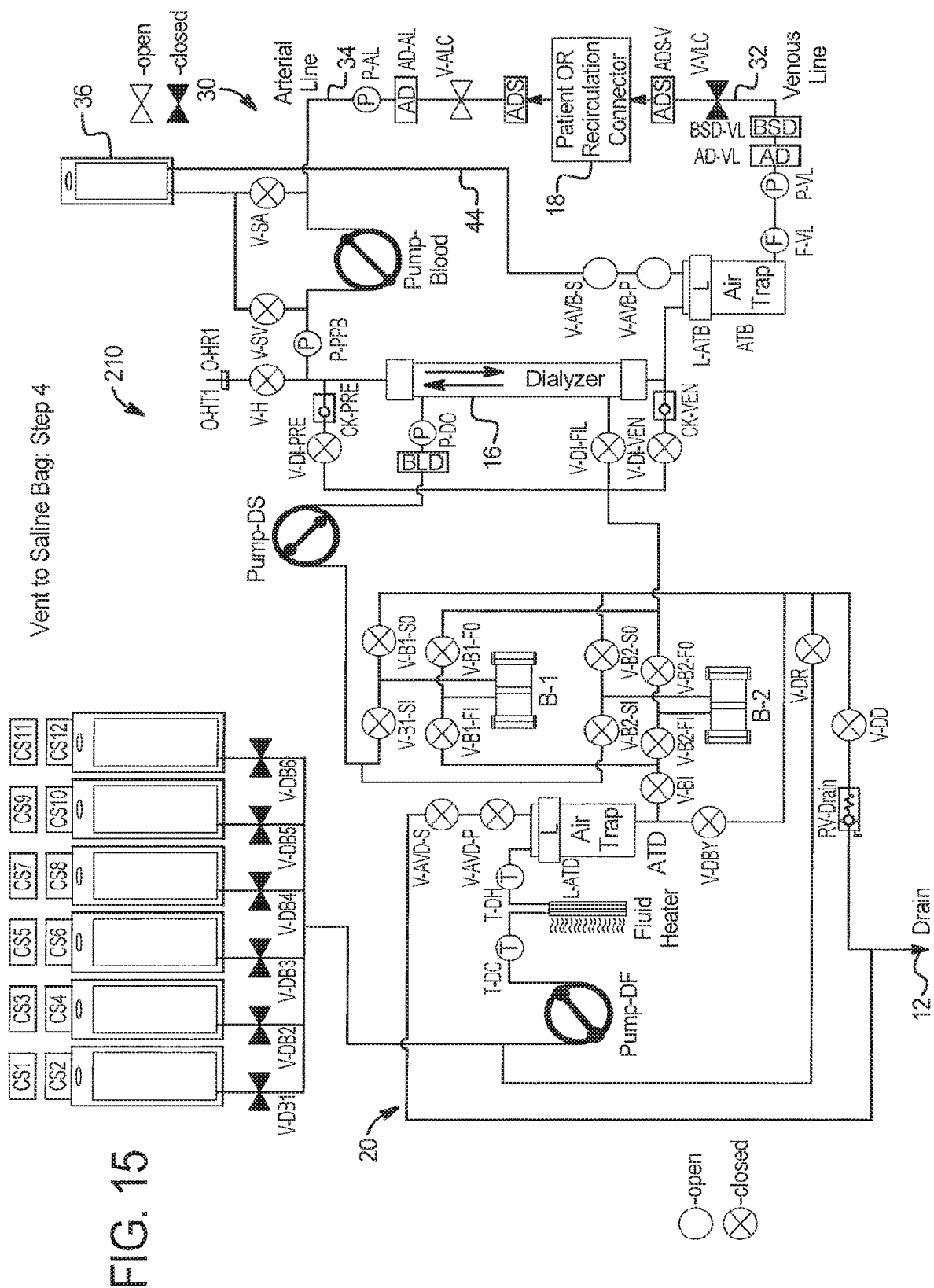

In step 4 at FIG. 15, system 210 prepares for blood prime by opening extracorporeal circuit air vent valves V-AVB-S and V-AVB-P, dialysate circuit air vent valves V-AVD-S and V-AVD-P, arterial patient line clamp V-ALC, and drain valve V-DD.

Figure 16:
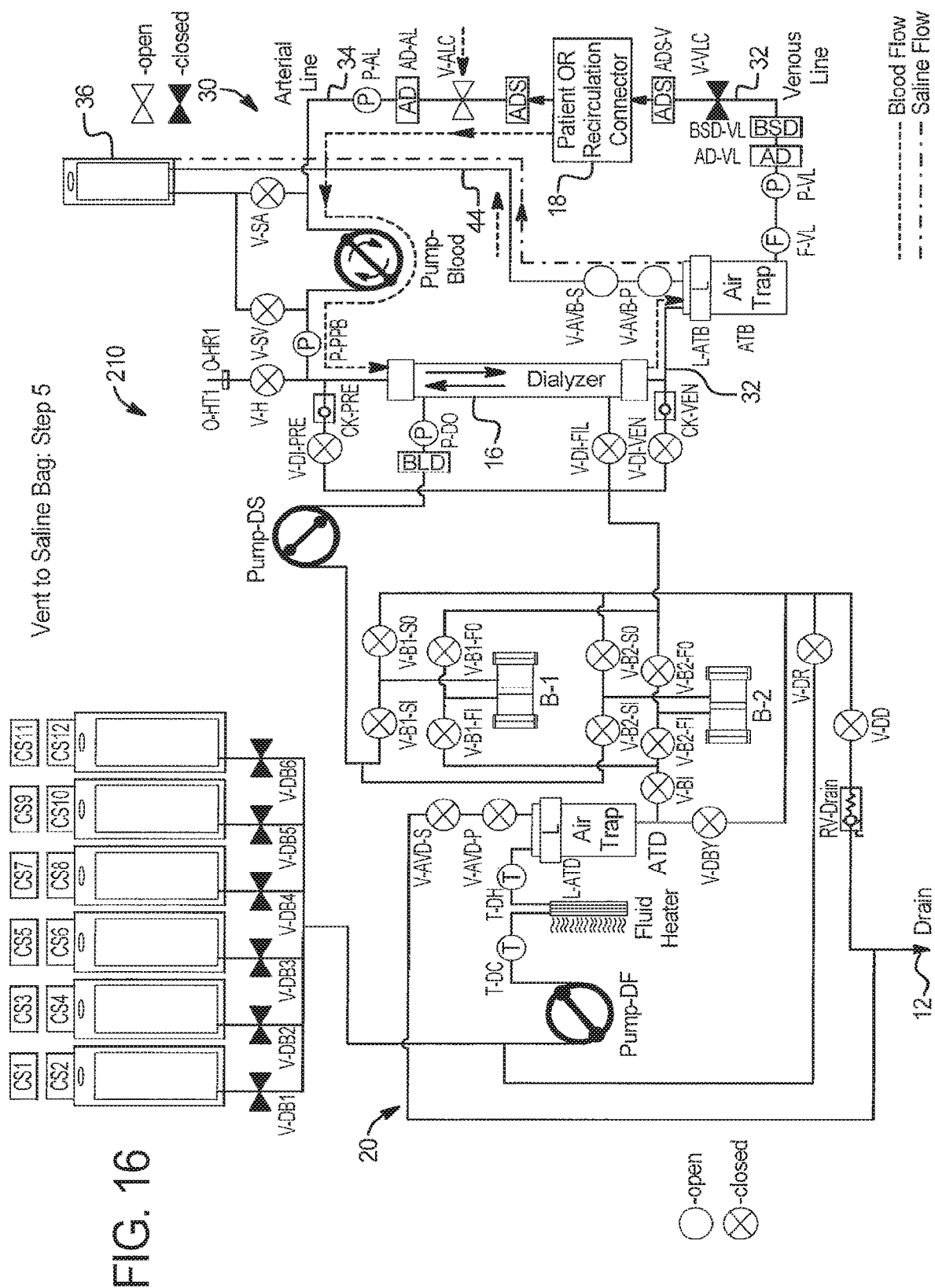

In step 5 at FIG. 16, system 210 runs PUMP-Blood in the clockwise direction for a specific number of pump strokes or period of time pulling blood from patient 18, through arterial line 34, dialyzer 16 and a portion of venous line 32 until blood reaches the beginning of the air trap ATB. System 210 can alternatively run the PUMP-Blood longer so blood moves into the air trap ATB, provided that system 210 can verify that blood does not escape air trap ATB during the blood priming process. The addition of a blood saline detector BSD as illustrated in FIG. 5 would facilitate this process.

In step 6 at FIG. 13, the system returns to safe state by closing all valves and patient line clamps and stopping all pumps.

Vent to Saline Bag—Fewer Air Vent Valves

Referring to FIG. 17, secondary air vent valves for the dialysate circuit V-AVD-S and extracorporeal circuit V-AVB-S have been removed. Primary vent vales V-AVD-P and V-AVB-P function primarily to maintain safety and may be used in combination with blood leak detectors BLD's as has been described herein. Since system 210 is closed to saline bag, however, it may be possible to use no vent valves.

Vent to Saline Bag—No Post-Pump Line

Referring again to FIG. 13, system 210 does not need separate pre- and post-blood pump saline lines (holding V-SV and V-SA) to the saline bag, so the post-pump saline line (holding V-SV) can be removed. Here system 210 uses the air trap fluid line 44 to also function as the post-pump fluid line.

Vent to Saline Bag—Extra Blood Detector

As with system 10 in FIG. 5, to prime the extracorporeal circuit 30 to a greater extent, system 210 can add a blood detector BLD in the post air-trap air vent line running to saline bag 36. An advantage here is that more of the air trap priming volume can be sent to the saline or other container.

Vent to Saline Bag—Other Container

Figure 18:
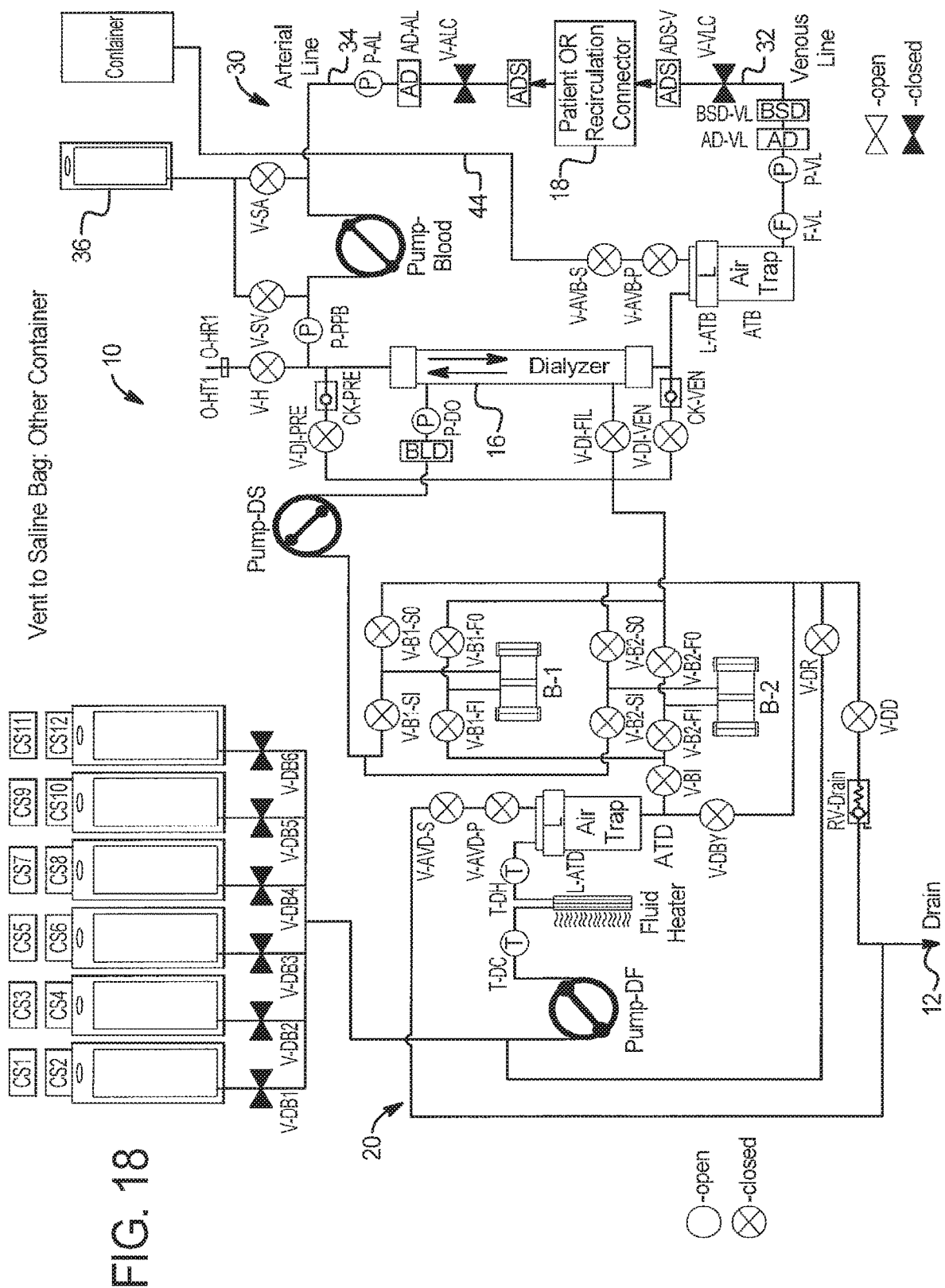

Referring to FIG. 18, the vent container does not have to be a saline bag 36. Vent line 44 can run instead to a different container, such as a used supply bag or a dedicated vent container.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
a dialysis fluid circuit;
a blood circuit including
an arterial line,
a venous line, and
an enclosure in fluid communication with the venous line, the enclosure configured to release air through a hydrophobic vent for priming the blood circuit;
a blood pump configured to pump fluid through at least the arterial line;
a first valve operable with the arterial line and a second valve operable with the venous line; and
a pumping and valving algorithm operated (i) to prime the blood circuit to remove air from the blood circuit through the hydrophobic vent, and (ii) to control the first and second valves and the blood pump to replace priming fluid with blood from a patient after priming the blood circuit.

2. The dialysis system of claim 1, wherein the enclosure includes an air trap.

3. The dialysis system of claim 1, wherein the hydrophobic vent communicates with the enclosure via a vent line.

4. The dialysis system of claim 1, wherein the priming fluid includes saline, heparin or dialysis fluid.

5. The dialysis system of claim 1, wherein the pumping and valving algorithm controls the first and second valves and the blood pump so that the blood from the patient replaces the priming fluid while both the arterial line and the venous line are connected to the patient.

6. The dialysis system of claim 1, which includes a dialyzer, the dialysis fluid circuit in fluid communication with a dialysis fluid compartment of the dialyzer, the blood circuit in fluid communication with a blood compartment of the dialyzer, and wherein the enclosure is located on the blood circuit side of the dialyzer.

7. The dialysis system of claim 1, wherein the enclosure is located along the venous line.

8. A dialysis system comprising:
a dialyzer including a dialysis fluid compartment and a blood compartment;
a dialysis fluid circuit in fluid communication with the dialysis fluid compartment of the dialyzer;
a blood circuit in fluid communication with the blood compartment of the dialyzer, the blood circuit including an arterial line and a venous line;
a priming fluid container connected to the blood circuit;
a blood pump configured to pump priming fluid from the priming fluid container through at least the arterial line;
an enclosure configured to release air through a hydrophobic vent when the blood pump pumps the priming fluid from the priming fluid container through at least the arterial line; and
an algorithm operated to use the blood pump to (i) prime the blood circuit using the priming fluid from the priming fluid container to remove air from the blood circuit through the hydrophobic vent, and (ii) replace the priming fluid with blood from a patient after priming the blood circuit.

9. The dialysis system of claim 8, wherein the enclosure includes an air trap.

10. The dialysis system of claim 8, wherein the hydrophobic vent communicates with the enclosure via a vent line.

11. The dialysis system of claim 8, wherein the priming fluid container is a saline container, and wherein the priming fluid is saline.

12. The dialysis system of claim 8, wherein the enclosure is located along the venous line.

13. The dialysis system of claim 8, wherein the priming fluid container is directly connected to the arterial line.

14. A dialysis system comprising:
 a dialyzer including a dialysis fluid compartment and a blood compartment;
 a blood circuit in fluid communication with the blood compartment of the dialyzer, the blood circuit including an arterial line and a venous line;
 a blood pump configured and arranged to pump fluid through the blood circuit;
 an enclosure connected along a flow path in fluid communication with the dialysis fluid compartment of the dialyzer, the enclosure configured to release air through a hydrophobic vent while the blood pump pumps fluid through at least the arterial line; and
 an algorithm operated to use the blood pump to (i) prime the blood circuit using the fluid to remove air from the blood circuit through the hydrophobic vent, and (ii) replace the fluid with blood from a patient after priming the blood circuit.

15. The dialysis system of claim 14, wherein the enclosure includes an air trap.

16. The dialysis system of claim 14, wherein the hydrophobic vent communicates with the enclosure via a vent line.

17. The dialysis system of claim 14, wherein the flow path in fluid communication with the dialysis fluid compartment of the dialyzer is part of a dialysis fluid circuit.

18. The dialysis system of claim 14, which includes a priming fluid container connected to the blood circuit, the enclosure configured to release air through a hydrophobic vent while the blood pump pumps priming fluid from the priming fluid container through the blood circuit.

19. The dialysis system of claim 14, which includes a first valve operable with the arterial line and a second valve operable with the venous line, wherein the algorithm is a pumping and valving algorithm operated to further control the valves and the blood pump to replace the priming fluid with blood from a patient after priming the blood circuit.

20. The dialysis system of claim 19, wherein the pumping and valving algorithm controls the first and second valves and the blood pump so that the blood from the patient replaces the priming fluid while both the arterial line and the venous line are connected to the patient.

\* \* \* \* \*